United States Patent [19]
Ozawa et al.

[11] Patent Number: 6,069,698
[45] Date of Patent: May 30, 2000

[54] OPTICAL IMAGING APPARATUS WHICH RADIATES A LOW COHERENCE LIGHT BEAM ONTO A TEST OBJECT, RECEIVES OPTICAL INFORMATION FROM LIGHT SCATTERED BY THE OBJECT, AND CONSTRUCTS THEREFROM A CROSS-SECTIONAL IMAGE OF THE OBJECT

[75] Inventors: Takeshi Ozawa, Tama; Mamoru Kaneko, Hanno; Akihiro Horii; Hitoshi Ueno, both of Hachioji; Sakae Takehana, Sagamihara; Hiroyuki Sangu; Isami Hirao, both of Hino; Hitoshi Mizuno, Koganei; Toshimasa Kawai; Hiroki Hibino, both of Hachioji; Hideyuki Adachi, Sagamihara; Hironobu Takizawa; Takefumi Uesugi, both of Hachioji; Masahiro Ohno, Kunitachi; Hidemichi Aoki, Tokorozawa; Jun Hiroya, Tokyo; Katsuichi Imaizumi; Eiji Yasuda, both of Hachioji; Yoshinao Oaki, Hino; Kenji Yoshino, Hachioji, all of Japan

[73] Assignee: Olympus Optical Co., Ltd., Japan

[21] Appl. No.: 09/141,430

[22] Filed: Aug. 27, 1998

[30] Foreign Application Priority Data

| Aug. 28, 1997 | [JP] | Japan | ................................... | 9-232999 |
| Aug. 28, 1997 | [JP] | Japan | ................................... | 9-233000 |
| Nov. 14, 1997 | [JP] | Japan | ................................... | 9-313924 |

[51] Int. Cl.$^7$ .................................................. G01B 9/02
[52] U.S. Cl. ........................ 356/345; 356/351; 356/354; 356/357
[58] Field of Search ................................... 356/345, 351, 356/354, 357

[56] References Cited

U.S. PATENT DOCUMENTS

| 5,120,953 | 6/1992 | Harris | .................................. | 250/227.2 |
| 5,161,053 | 11/1992 | Dabbs | ...................................... | 359/384 |
| 5,321,501 | 6/1994 | Swanson et al. | ........................ | 356/345 |
| 5,383,467 | 1/1995 | Auer et al. | ............................... | 128/664 |
| 5,459,570 | 10/1995 | Swanson et al. | ........................ | 356/345 |
| 5,582,171 | 12/1996 | Chornenky et al. | .................. | 128/653.1 |
| 5,601,087 | 2/1997 | Gunderson et al. | ..................... | 128/664 |

FOREIGN PATENT DOCUMENTS

| 6511312 | 12/1994 | Japan . |
| 92/19930 | 11/1992 | WIPO . |

OTHER PUBLICATIONS

G.J. Tearney, et al., "In Vivo Endoscopic Optical Biopsy with Optical Coherence Tomography," Science, vol. 276, Jun. 27, 1997, pp. 2037–2039.

D.L. Dickensheets, et al., "Micromachined Scanning Confocal Optical Microscope" Optics Letters, vol. 21, No. 10, May 15, 1996, pp. 764–766.

*Primary Examiner*—Robert H. Kim
*Assistant Examiner*—Andrew H. Lee
*Attorney, Agent, or Firm*—Ostrolenk, Faber, Gerb & Soffen, LLP

[57] ABSTRACT

A low coherence beam emitted by a low coherence light source is split into two portions. One portion is transmitted from the outward end of a first single mode fiber via a detachable connector to a beam scanning probe, and then to a biological tissue; and the other is transmitted from an optical coupler placed midway along the light path via a second single mode fiber to a light path modifier. The light path modifier includes a galvanometer mirror to modify the light path length in accordance with a scan range, and a uniaxial stage to adjust the light path length to absorb the variation in lengths of different beam scanning probes. The light path is adjusted by the uniaxial stage such that the beam interference is detected for the scan range, to ensure stable acquisition of tomographic images.

35 Claims, 15 Drawing Sheets

OPTICAL IMAGING APPARATUS WHICH RADIATES A LOW COHERENCE LIGHT BEAM ONTO A TEST OBJECT, RECEIVES OPTICAL INFORMATION FROM LIGHT SCATTERED BY THE OBJECT, AND CONSTRUCTS THEREFROM A CROSS-SECTIONAL IMAGE OF THE OBJECT

BACKGROUND OF THE INVENTION

1. Field of the Invention

This invention relates to an optical imaging apparatus which radiates a low coherence light beam onto a test object, receives optical information from light scattered by the object, and constructs therefrom a cross-sectional image of the object.

2. Description of the Related Art

Recently, for diagnosis of a sick biological tissue, optical CT apparatuses have been developed which provide optical information regarding the internal structure of that tissue, in addition to imaging apparatuses which provide optical information regarding the surface condition of that tissue.

The optical CT apparatus provides cross-sectional images of a living body by delivering pulses with a duration of some pico-seconds, thereby obtaining the information of its internal structure, but a laser light source which is required for delivering such ultra-short pulses with a duration of pico-second order is expensive, large in size and cumbersome for handling.

Recently, interference type OCT (optical coherence tomography) apparatuses which provide sectional images of a test object using a low coherence light beam is disclosed, for example, in Japanese Unexamined Patent Publication No. 6-511312.

In this particular previous example, however, no attention has been paid to the variation in length of individual optical probes which is often encountered when an old probe is replaced with a new one. Such variation in length may narrow the range within which acquisition of sectional images is possible, and, in worst cases, may completely annihilate the possibility of obtaining sectional images.

Further, it is desirable for the probe, when it is used in a body cavity, to operate in conjunction with an endoscope. In such case, it would be convenient if the probe could be inserted through a forceps channel of that endoscope. But, no previous apparatuses have been so designed as to allow their adjunct probes to be exchanged as appropriate according to the length of forceps channel of an endoscope to be used in cooperation.

SUMMARY OF THE INVENTION

The object of this invention is to provide an optical imaging apparatus which can securely obtain cross-sectional images of a test object even after optical probes are exchanged.

Another object of this invention is to provide an optical imaging apparatus which not only allows the optical probe to be sufficiently slender to be inserted in a body cavity, but also ensures acquisition of high-resolution optical cross-sectional images of a test object.

A further object of this invention is to provide an optical imaging apparatus which not only enables the insert to be thinned, but also ensures a stable optical scanning, thereby obtaining stable cross-sectional images based on the stable optical scanning.

The optical imaging apparatus of this invention comprising:

a light source to generate a low coherence light beam;

an optical probe incorporating a sample beam transmitting means made of a single-mode fiber which transmits the sample beam comprising said low coherence light beam to be radiated onto a test object, and the sample beam reflected by the test object;

a detecting means which is reversibly attached to said optical probe through an optical connector, allows said reflected beam and the reference beam comprising said low coherence light beam to interfere with each other, and detects an interference fringe resulting from the interference;

an image signal generating means to generate image signals based on signals provided by said detecting means;

a first transmission time altering means which alters the transmission time of reference beam in accordance with the scanning range so that the interference position between said reflected beam and reference beam is scanned in the axial direction with respect to the optical axis; and a second transmission time altering means which alters the transmission time of the reference beam in accordance with the length of light path of said sample beam transmitting means, which ensures secure acquisition of cross-sectional images of the test object within a predetermined scanning range, even after optical probes are exchanged which may have light paths different in length owing to a production variation, by appropriately adjusting the transmission time using the second transmission time altering means, thereby absorbing the adverse effects due, for example, to such a production variation.

Other features and advantages of this invention will become thoroughly obvious in the process of following description.

BRIEF DESCRIPTION OF THE DRAWINGS

FIG. 1 shows the composition of an optical imaging apparatus representing the first embodiment of this invention; FIG. 2 shows an endoscope through which the first embodiment is inserted; FIG. 3 shows the rear end of optical scanning probe device constituting the first embodiment; FIG. 4 shows the overall composition of optical scanning probe device; and FIG. 5 shows the composition of a variation of the light path length altering means.

FIG. 6 shows the composition of an optical imaging apparatus representing the second embodiment of this invention; FIG. 7 gives a flat view of a light path modifying means; and FIG. 8 gives a sectional view of the same cut along line A–A' of FIG. 7.

FIG. 9 shows the composition of an optical imaging apparatus representing the third embodiment of this invention; and FIG. 10 shows the structure of an optical delay line.

FIG. 11 shows the composition of an optical imaging apparatus representing the fourth embodiment of this invention; FIG. 12 shows the structure of the handle of probe of a first variation; FIG. 13 shows the composition of the tip of a beam scanning probe of a second variation; and FIG. 14 shows the mechanism how the light path is altered in a third variation.

FIG. 15 shows the composition of the tip of beam scanning probe; and FIG. 16 shows the composition of a scanning device mounted to the tip of beam scanning probe of FIG. 15.

FIG. 17 shows the composition of the tip of beam scanning probe; FIG. 18 shows the composition of a piezo-electric actuator to move the entire scanning unit body; and FIG. 19 gives graphs to illustrate how the scanning unit of FIG. 17 operates.

FIG. 20 gives a sectional view to illustrate the tip of beam scanning probe device; and FIG. 21 gives a sectional view to illustrate the tip of a variation of beam scanning prove device of FIG. 20.

Figure 1:
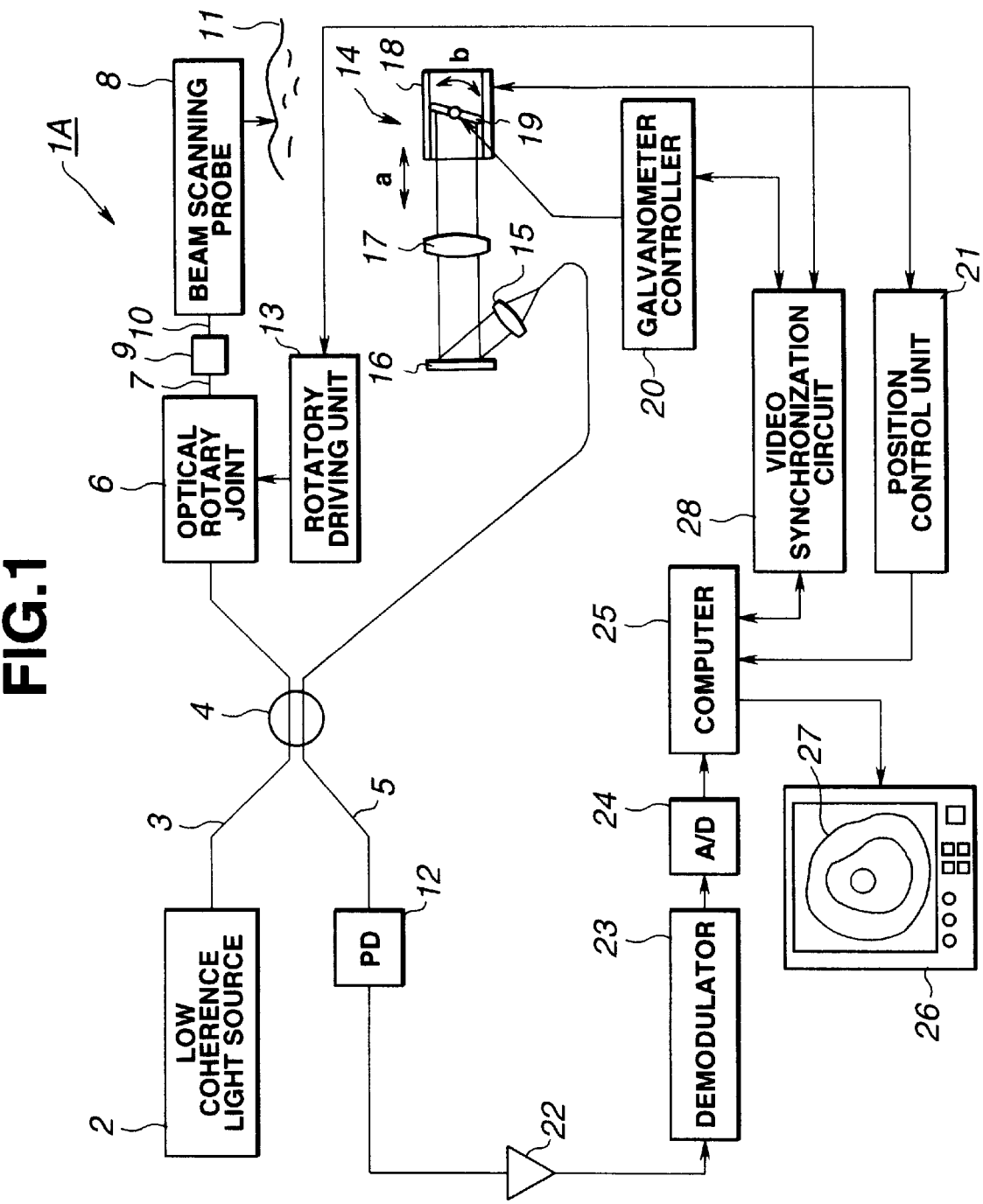
FIGS. 1 to 5 relate to the first embodiment of this invention.

DESCRIPTION OF THE PREFERRED EMBODIMENTS (The first embodiment)

An optical imaging apparatus 1A (optical tomography apparatus) includes a low coherence light source 2 such as a super-bright light emitting diode (to be abbreviated as SLD hereinafter). This low coherence light source 2 is characterized by giving a low coherence light beam which is so resistive to interference that, assumed that it has a wavelength, for example, of 1300 nm, it narrowly presents an interference only when the distance difference to cause an interference exceeds a magnitude as small as, say, 17 $\mu$m. Let's illustrate it taking an example. Assume that the beam from this source is split into two components to take different light paths, and the two are recombined later. If the two light paths the two beam components taken from the split point to the recombination point are different in length from each other by as small as about 17 $\mu$m or less, then the two beams are detected as beams interfering with each other, while when the two light paths in question are separated by more than above range, the two beams do not interfere with each other.

A beam from this low coherence light source 2 is incident on one tip of a first single mode fiber 3, and is transmitted to the other end (outward end surface).

This first single mode fiber 3 is optically connected with a second single mode fiber 5 at an optical coupler 4 inserted midway. Hence, the beam is split into two components at this optical coupler and the components are then transmitted separately.

Into the outward tip (away from the optical coupler 4) of first single mode fiber 3, is inserted an optical rotary joint 6 with a non-rotary section and a rotary section which establishes a connection permitting the transmission of light; to the outward tip of a third single mode fiber passing through the optical rotary joint 6 is reversibly attached a connector 9 of a beam scanning probe 8; and into the beam scanning probe 8 is inserted a fourth single mode fiber 10 which is driven into rotation; and the beam from the low coherence light source 2 is transmitted (guided) through the fourth single mode fiber 10.

The thus transmitted beam emanates from the outward tip of beam scanning probe 8 to radiate onto a biological tissue 11 while scanning over the latter. A part of the reflected rays scattered from the surface of or from the interior of biological tissue 11 is picked up by the same probe to be sent back along the same path to the first single mode fiber 3 where a part of the reflected beam is transferred to the second single mode fiber 5 by the optical coupler 4; and that part, emanating from one end of second single mode fiber 5 and is incident on, for example, a photo diode serving as a photosensitive detector. The rotary section of optical rotary joint is put into rotation by a rotary driving unit 13.

The second single mode fiber 5 has, on the outward side from the optical coupler 4, a light path modifying mechanism 14 which alters the light path for the reference beam. This light path modifying mechanism has a first light path modifying means which speedily modifies the light path in accordance with the scan range when a biological tissue 11 is scanned by the beam scanning probe 8 for a specified length in the depth direction, and a second light path modifying means which, when beam scanning probes 8 having varying lengths are exchanged, can modify the length of the light path in accordance with the given variation to absorb that variation.

A grating 16 is placed opposite to the tip of second single mode fiber 5 with a lens 15 in between; placed opposite to the grating (diffraction grating) 16 with a lens 17 in between is a uniaxial stage 18 which can freely move in the direction of the light path, thereby to modify the length of the light path as indicated by the symbol a in the figure; on the uniaxial stage 18 is mounted a galvanometer mirror 19 or an element of the first light path modifying means which can rotate by a minute angle; and this galvanometer mirror 19 readily rotates under the control of a galvanometer controller 20 in the directions indicated by the symbol b.

This galvanometer mirror 19 is implemented to reflect light with the mirror of galvanometer which, when given a driving signal comprising an alternating current, puts into fast rotatory vibrations the mirror which is fixed to its movable part.

Then, the light path taken by the beam emanating from the end of second single mode fiber 5, and reflected by the galvanometer mirror 19 alters, through these rotatory vibrations, by a specified amount in correspondence with the depth by which a biological tissue 11 is scanned.

To put it otherwise, the galvanometer mirror 19 acts as a first light path modifying means which is necessary for acquisition of cross-sectional images of a tissue in the direction of depth. The light path modifying means based on the galvanometer mirror 19 is disclosed in SCIENCE, Vol. 276, 1997, pp. 2037–2039.

By the way, the uniaxial stage 18 further includes the second light path modifying means which reversibly adjusts the length of light path with a sufficient adjustable range to absorb the variation in length of individual beam scanning probes when probes are exchanged; and the same executes an offset control function to collect an image from a desired position by appropriately adjusting the light path. (Given, for example, an image from the surface of a biological tissue 11is desired, and that the tip of beam scanning probe 8 does not contact with that surface, altering the light path by the uniaxial stage 18 in such a way as to cause the beam reflected from the surface to produce an interference makes it possible to collect an image from that surface).

This uniaxial stage 18 has a motor for movement, and can move in the direction as indicated by the symbol a in the figure by applying a driving signal to the motor via a position control unit 21.

The beam whose light path has been modified by this light path modifying mechanism 14 is combined with the beam leaked from the first single mode fiber 3 at the coupler 4 placed at midway of second single mode fiber 5, and the two beams are received together by a photo diode 12.

The second single mode fiber 5 is constructed such that, when the uniaxial stage 18 is placed in the middle of its movable range, the light path one beam takes from the optical coupler 4 through the fourth single mode fiber 9 and the beam scanning probe 8 to a biological tissue 11 is comparable in length to that of the light path the other beam takes, after having passed through the second single mode fiber 5 and been reflected by the galvanometer mirror 19 on the uniaxial stage 18.

The uniaxial stage 18 is adjusted in position in accordance with the beam scanning probe 8 being currently used, thereby to absorb the variation in length inherent to this particular beam scanning probe 8; at the same time the galvanometer mirror 19 is put into rapid rotations or vibrations thereby to alter the light path of reference beam periodically; and thus the beam reflected from a certain desired spot of the biological tissue 11 in the direction of depth whose light path is nearly equal to the path of reference beam will interfere with the reference beam while beams reflected from other spots of the same biological tissue different in depth will not interfere with the reference beam.

The beams received by aforementioned photo diode 12 undergo a photo-electric conversion to produce a signal which is, after being amplified by an amplifier 22, delivered to a demodulator 23. The demodulator 23 executes a demodulation treatment to extract signal components contained only in the beams interfering each other, and the output is fed through an A/D converter 24 to a computer 25. The computer 25 produces imaging data representing a tomographic image, and delivers them to a monitor 26 thereby to cause the monitor to display an OCT image 27 on its display surface.

The computer 25 is connected to a position control unit 21 and controls the position of uniaxial stage 18 via the position control unit 21. The computer 25 is also connected to a video synchronization circuit 28, and stores tomographic image data into an internal memory in synchrony with video synchronization signals generated during the formation of images.

The video synchronization signals generated by the video synchronization circuit 28 are delivered to both of the galvanometer controller 20 and rotary driving unit 13; the galvanometer controller 20, for example, generates driving signals in synchrony with the video synchronization signals (more concretely, with, of the two kinds of video synchronization signals including fast and slow signals, first fast video signals) while the rotary driving unit 13 generates driving signals in synchrony with the video synchronization signals (more concretely, with second slow video synchronization signals), thereby to put the rotary driving unit 13 into rotation and to scan the beam spot in the circular direction.

Figure 2:
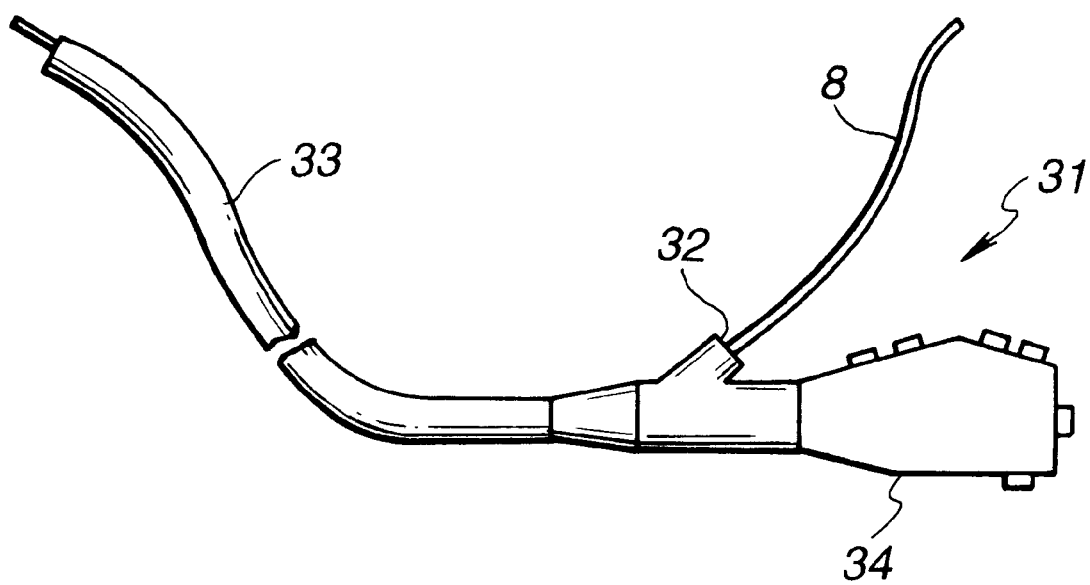

As shown in FIG. 2, the beam scanning probe 8 of the first embodiment can be inserted from the forceps insertion port 32 of an endoscope 31 into a forceps insertion channel and its tip can be protruded from the opening prepared on the outward tip of the same channel.

This endoscope 31 has such a slender insert 33 that the insertion of its tip into a bodily cavity may be achieved easily, and at the rear end of this insert 33 is provided a thickened handle 34. Close to the rear end of this insert 33 is prepared the forceps insertion port 32, and the forceps insertion port 32 communicates with the forceps insertion channel.

A light guide not illustrated here is inserted into the insert 33; the light receiving end thereof is connected with a light source; and light from the latter is allowed to emanate from an illumination window prepared at the tip of insert 33 to illumine a lesion to be examined or the like. Further, an observation window is prepared close to the illumination window; and to the observation window is connected an object observing optical system so that one can observe the lesion illumined in the manner as described above through the optical system.

While observation proceeds through the object observing optical system mounted to the tip of endoscope 31, the beam scanning probe 8 radiates a low coherence light beam on a part of interest of a biological tissue such as a lesion, collects data for tomographic images of the interior of biological tissue, and delivers them for processing so that an OCT image 27 thereof is displayed on the display surface of monitor 26.

The composition of beam scanning probe 8 will be described below with reference to FIGS. 3 and 4.

Figure 3:
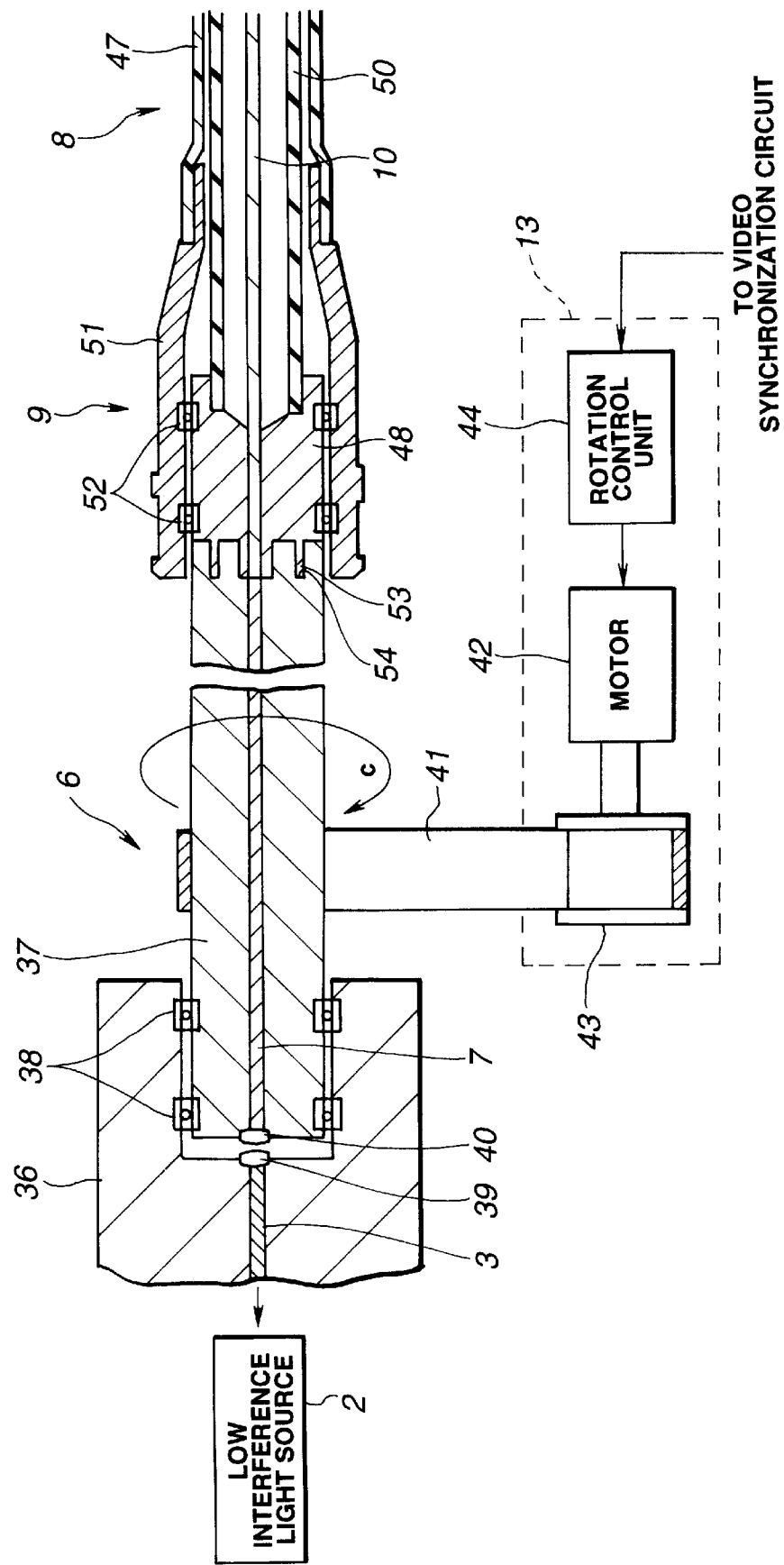

The outward end of first single mode fiber 3 is optically coupled with fourth single mode fiber 10 inserted into the beam scanning probe 8 through the third single mode fiber 7 staying in the optical rotary joint 6 shown in FIG. 3.

The first single mode fiber 3 has a rotor socket 36 at its tip; to the concavity of rotor socket 36 is fitted a rotor 37; and the rotor 37 is held by two bearings 38 inserted between above two elements rotatably (with respect to the bearings 36 which remain motionless).

Along the central axes of rotor socket 36 and rotor 37 are inserted the first single mode fiber 3 and the third single mode fiber 7 respectively; and at the ends of both fibers 3 and 7 which face to each other are placed convex lenses 39 and 40 so that an efficient transmission of beams is achieved between the motionless fiber 3 and the rotating fiber 7.

The rotor 37 is also connected, for example through a belt 41, to the pulley 43 of a motor which forms an element of the rotary driving unit 13. When the motor 42 is put into rotation, the rotor 37 is also put into rotation as indicated by arrow c in the figure and the third single mode fiber 7 is put to rotation in association. The motor 42 rotates at a constant speed being governed by motor driving signals provided by a rotation controller 44.

To the tip of rotor 37 is reversibly fitted a connector 9 which has been placed at the rear end of beam scanning probe B.

Figure 4:
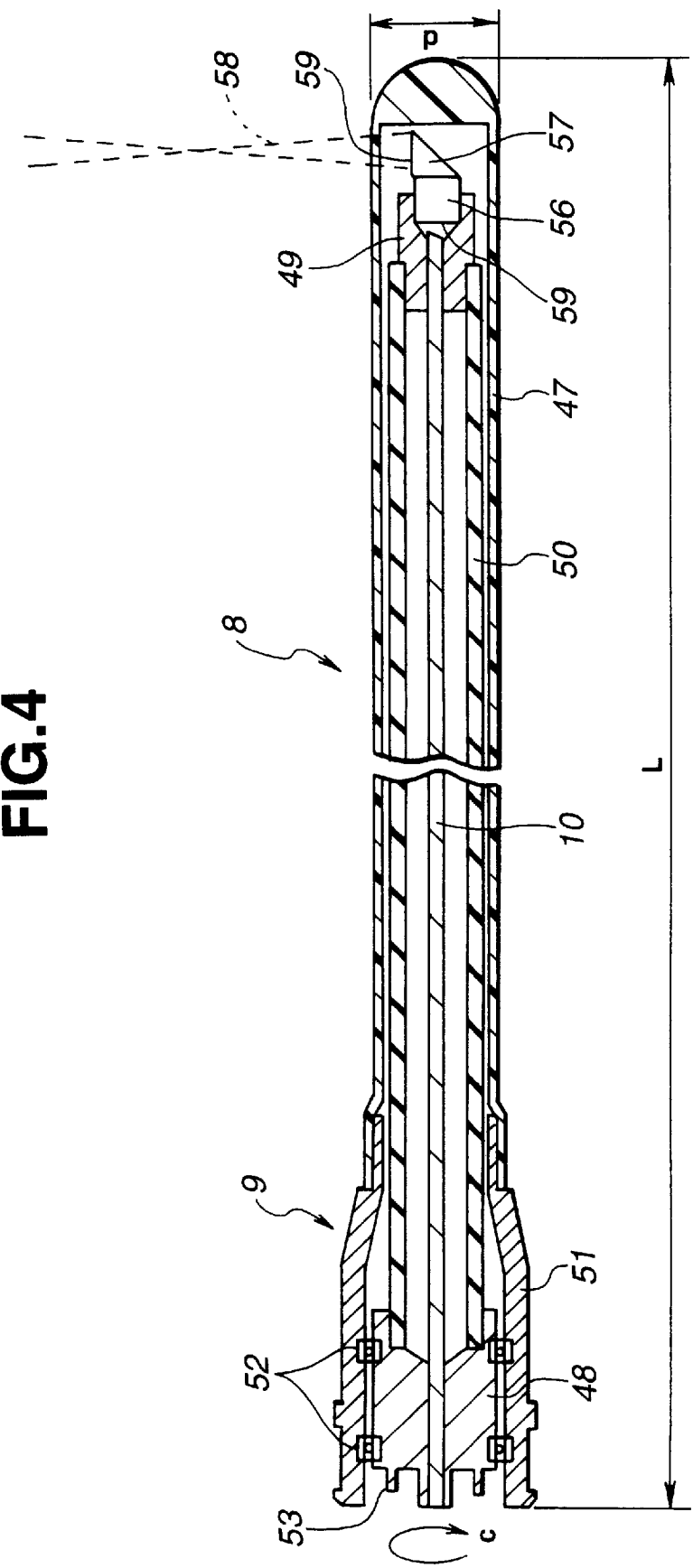

As shown in FIG. 4, the beam scanning probe 8 puts the fourth single mode fiber 10 along the central axis of slender, cylindrical sheath 47 which acts as an outer tube of the probe; the rear and front ends of fourth single mode fiber 10 are fixed respectively to the connector body 48 and the tip body 49; and the fourth single mode fiber 10 is covered with a flexible shaft 50 which is made of a hollow, soft material to transmit a rotatory force. The inner diameter of this flexible shaft 50 is slightly larger than the outer diameter of fourth single mode fiber 10.

The fourth single mode fiber 10 has a core diameter of, for example, about 9 $\mu$m.

The sheath 47 is made of a transparent, light transmissive (to a low coherence light beam) tube composed, for example, of polymethyl pentane, polyamide, FEP, TPFE, PFA or the like. The flexible shaft 50 is a coil which is composed of a wire densely wound in a duplicate or triplicate manner, has a flexibility, and is capable of efficiently transmitting a force applied to one end of it to the other. The rear and front ends of this flexible shaft 50 are also fixed to the connector body 48 and tip body 49, respectively.

To the rear end of sheath 47 is firmly fixed a cylindrical connector cover 51 which forms an element of the connector 9, and in the interior of connector cover 51 the columnar connector body 48 is rotatably held by two bearings 52. Into the hole prepared along the central axis of connector body 48, is inserted the rear end of fourth single mode fiber 10, and fixed there with an adhesive or the like.

This connector body 48 has projections 53 on its rear end; the rotor 37 has cavities 54 on its front end which are to engage with the projections 53. When the rotor 37 is put into rotation while the concavities and projections being fitted to each other, the connector body 48 is also put into rotation. This rotatory force is conferred to the rear end of flexible shaft 50, transmitted through the flexible shaft body 50 down to its tip, and used to rotate the tip body 49 attached to the same tip.

As shown in FIG. 4, the tip of fourth single mode fiber 10 is inserted through the hole prepared along the central axis of tip body 49 and fixed there with an adhesive or the like; and the front port prepared on the front end surface of fourth single mode fiber 10 is slightly widened to receive a cell foc lens 56 (GRIN lens) to converge rays emanating from the front end of fourth single mode fiber 10 onto a specified position. To the front end surface of this GRIN lens 56 is fixed a micro prism 57 which is to modify the path of a beam by reflecting it. The prism is fixed with an adhesive or the like.

Rays, being guided by the fourth single mode fiber 10 and adjusted to take a light path lengthened by a specified amount, are converged by the GRIN lens 56; the rays are reflected by the micro prism 57 to be bent perpendicularly; and they are allowed to pass through the transparent sheath 47 and converged into a radiating beam 58 (having a low interference property) outside the tip. The beam has a flux diameter of about 10 to 30 μm at a focusing point having a specified distance.

The fourth single mode fiber 10 has its front end cut obliquely, to prevent light directly reflected by the rear surface of GRIN lens 56 from entering that front end.

Anti-reflection films 59 consisting of an anti-reflection material are formed on the rear surface of the GRIN lens 56 and on the front surface of micro prism 57, to suppress light reflected from those surfaces.

The sheath 47 has its tip shaped like a semicircle and closed. The beam scanning probe 8 of this example has a total length of about 2000 mm, and the sheath has a diameter of 2.4 mm.

Next, the operation of this example will be described.

Illuminating light generated by an endoscope light source not illustrated here is guided by the light guide of endoscope 31, to illumine a biological tissue 11 from the illumination window prepared at the tip of insert 33. Light carrying the image of biological tissue 11 thus illumined passes through the observation window, and is focused through the object observing optical system onto a solid image fixing element; and processed by the video processor to present an endoscopic image on the display monitor.

For a low coherence light beam to display a tomographic image, the beam scanning probe 8 is inserted into a forceps insertion port 32 of an endoscope 31 as shown in FIG. 2, and is allowed to pass through the forceps channel until its tip protrudes from the tip of the latter.

The connector 9 at the rear end of beam scanning probe 8 is connected to the rotor 37 at the front end of optical rotary joint 6; then the optical imaging apparatus 1A as depicted in FIG. 1 is completed ready for use.

During this operation, the light path may vary slightly according to individual variations in length of beam scanning probes 8 when they are exchanged for each other. Even if, under this condition, the galvanometer mirror 19 is put into rotatory vibrations being triggered by driving signals from the galvanometer controller 20; the light path of reference beam reflected by the galvanometer mirror 19 is altered rapidly and periodically therewith; and tomographic image data of a biological tissue 11 in the depth direction are obtained, a number of difficulties will be encountered because the light path of beam scanning probe 8 and the light path of reference beam are not properly adjusted with respect to each other. Assume, for example, that the galvanometer mirror 19 is so adjusted as to lengthen the light path from the shortest state, then during the shift it is found that tomographic image data of a tissue 11 are obtained only when the light path falls in the middle of adjustable range (because the sample beam reflected from a too shallow surface level does not fall in the range where interfere with the reference beam reflected by the galvanometer mirror 19 is possible, and hence does not provide tomographic image data thereof) or conversely the sample beam reflected from a too deep level will not provide tomographic image data thereof for the same reason.

To cope with such inconvenience, in this example, the computer 25 moves via the position control unit 21 the uniaxial stage 18 as appropriate in the directions as indicated by symbol a in the figure. To put it concretely, it moves the stage so that the light path is gradually lengthened from the shortest position (with regard to the apparatus of FIG. 1, the stage is shifted from left to right). During this operation, the galvanometer mirror 19 is put into speedy rotatory vibrations as in ordinary operation.

During this movement, although initially no OCT images 27 of a tissue 11 appear on the monitor 26, interference pattern representative of the structure of tissue 11 is detected as soon as the light path the reference beam takes is sufficiently equal in length to that of the beam on the side of the beam scanning probe 8; the interference pattern is displayed as OCT images 27 of the tissue 11 on the monitor 26, and the OCT images on display become increasingly widened.

When, for example, the scanning range reaches a specified depth from the surface of biological tissue targeted where a part of interest exists, the operator feeds a command by striking appropriate keys on a key board not illustrated here to the computer to halt the further movement of uniaxial stage 18.

Through this operation, one can securely obtain images of a biological tissue under study from the surface down to a desired depth as OCT images 27 on the monitor 26.

According to this example, it is possible to quickly alter the light path of reference beam in accordance not only with the light path of sample beam having a certain scan range, but with the path of a given beam scanning probe 8 currently used. Hence, even when beam scanning probes 8 are exchanged, it is possible to avoid a situation where no or practically no tomographic images can be obtained, and thus to securely obtain tomographic images of the desired scan range.

With the beam scanning probe 8 of this example, the fourth single mode fiber 10 placed along the central axis of the probe is put into rotation, thereby to rotate the GRIN lens 56 and the micro prism 57 fixed to its outward tip in association, and this makes it possible to securely scan a low coherence light beam in the direction perpendicular to the central axis of beam scanning probe 8, and thus to ensure a secure acquisition of tomographic images in the direction of depth and having a radial extension in a two-dimensional space.

To put it more concretely, by scanning a beam radially, for example, in a narrow space limited by a tubular cavity, and obtaining therewith radially extended tomographic images of a lesion, it is possible not only to observe the surface condition of the lesion with the endoscope 31, but also to collect tomographic images representing the internal morbid condition as well which may be useful for the proper diagnosis of that lesion.

To introduce another practical use of this invention, for example, when a biological tissue 11 in a body cavity, particularly its morbid part or the like is studied through the endoscope 31, and attention is focused on its internal condition, the lateral surface of outward tip of beam scanning probe 8 is placed close to the part of interest (for example, the lateral surface of outward tip of beam scanning probe 8 is placed nearly parallel to the part of interest); the part is scanned radially; and tomographic images thereof are collected in the manner as described above.

Further, it is possible to display, instead of a tomographic image extending radially in a circle, an image representing a limited range including only the morbid part of interest on the monitor 26. This method of display can be employed even in a tubular cavity having a wide space. This method of display can also be employed in a narrow tubular cavity when a detailed image of a limited section of a lesion is required.

Furthermore, the apparatus may be modified such that the rotation speed (scanning speed in other words) can vary according to given observation conditions, for example, where tomographic images of a lesion extending radially in a circle are required, or where tomographic images of a lesion extending in a limited arc are required.

Figure 5:
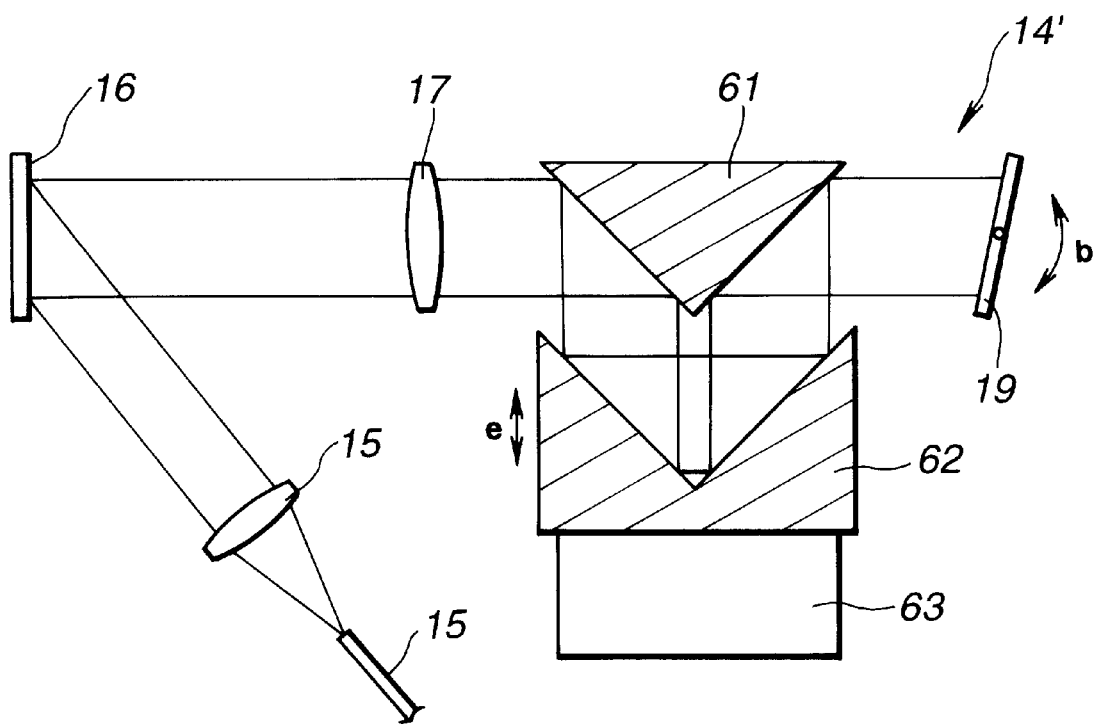

The light path modifying means of the first embodiment consists of the uniaxial stage 18, and the galvanometer mirror 19 installed in that uniaxial stage. However, the same function may be achieved without the use of uniaxial stage, as seen from the variant light path modifying means 14' shown in FIG. 5, which achieves the same object by following means. A mirror 61 like a triangular prism is inserted on the light path between the lens 17 and the galvanometer mirror 19; another reflective mirror 62 is placed on the light path which a beam would take when reflected by either one of the inclined surfaces of mirror 61; the mirror 62 is moved in the directions as indicated by symbol e along the light path formed between itself and the mirror 61 placed opposite, being triggered by a driving signal applied to a linear actuator 63; and therewith the variation in light path length may be absorbed each time beam scanning probes 8 are exchanged.

Although it was described above that the uniaxial stage 18 moves the galvanometer mirror 19, or alternatively the linear actuator 63 moves the mirror 62 through an electrical driving signal, the movement in question may take place manually.

(The second embodiment)

Figure 6:
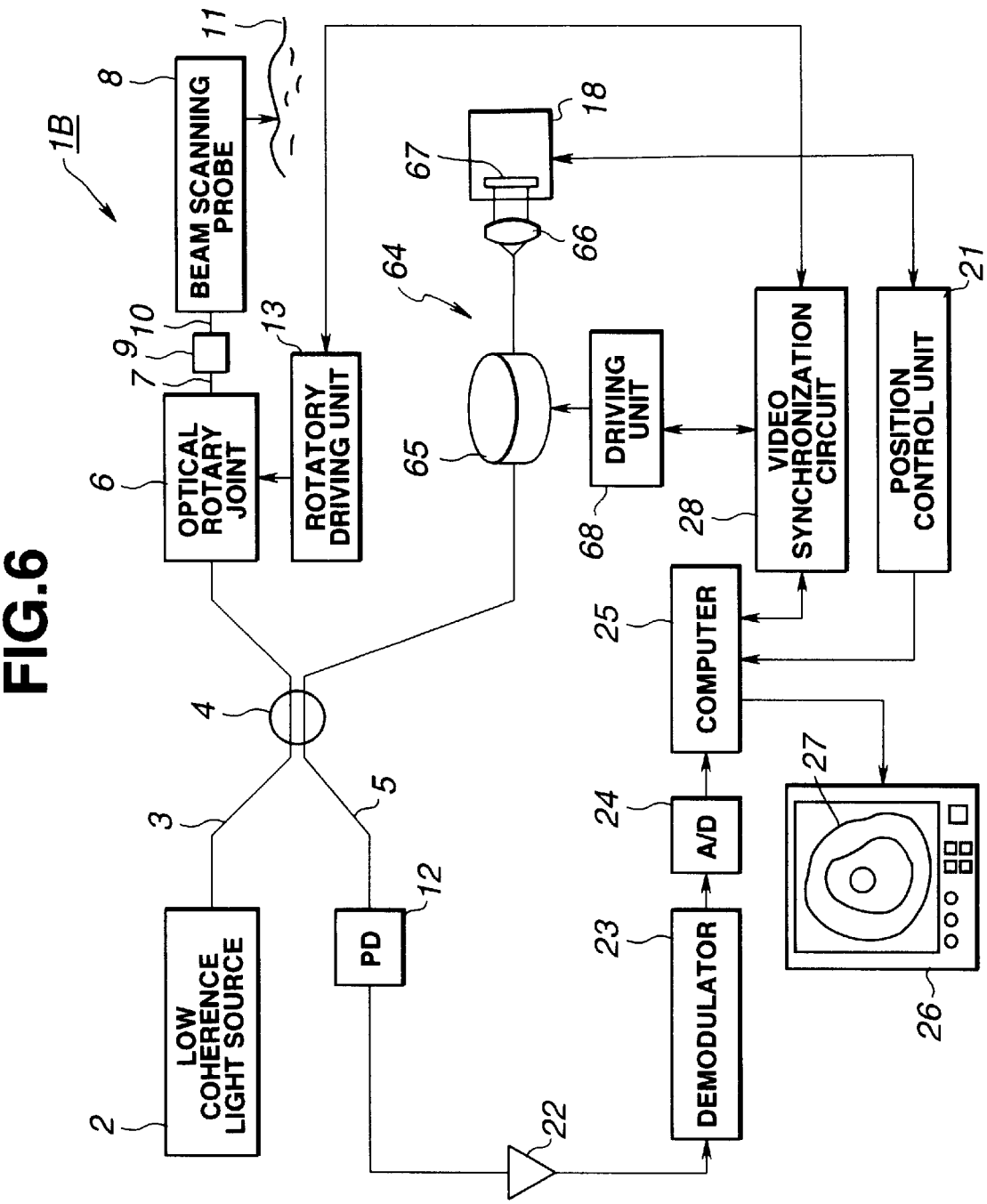
FIGS. 6 to 8 relate to the second embodiment of this invention.

The optical imaging apparatus 1B of the second embodiment as shown in FIG. 6 employs a more widely applicable transmission time altering mechanism 64 having a different composition from the light path modifying means used by the optical imaging apparatus 1A of the first embodiment shown in FIG. 1 to modify the light path length of reference beam.

To put it more in detail, the outward tip of second single mode fiber 5 is wound around a disc-like piezo element 65 which serves as a first transmission time altering means; the outward end is allowed to extend from the piezo element 65; a lens 66 is placed opposite to that outward end; and opposite to this lens 66 is placed a mirror 67 installed in a uniaxial stage 18 which serves as a second transmission time altering means.

The uniaxial stage 18 is to absorb individual differences in light path length of beam scanning probes 8; its moving distance can be adjusted by the position control unit 21; and the piezo element receives a driving signal comprising an alternating current from the driving unit 68.

Figure 7:
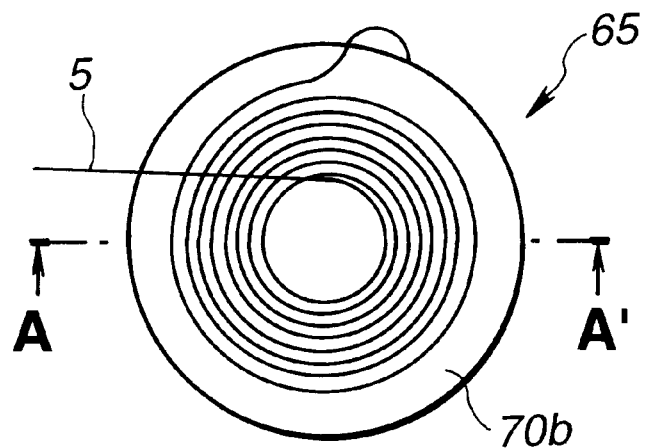
Figure 8:
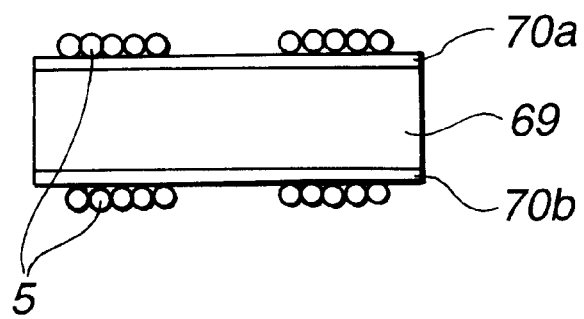

As shown in FIGS. 7 and 8, the piezo element 65 around which the second single mode fiber 5 has been wound has electrodes 70a and 70b on the upper and lower surfaces of its disc-like piezo plate 69; and the second single mode fiber 5 is wound over the electrodes 70a and 70b like concentric rings and is bonded to the surfaces of those electrodes 70a and 70b with an adhesive or the like.

An AC driving signal from the driving unit 68 is given across the two electrodes 70a and 70b; application of this driving signal results in elongation/contraction of the piezo plate in the radial direction; as if being excited by this elongation/contraction, the second single mode fiber 5 wound in concentric rings are also elongated/contracted; in association with this elongation/contraction, the light path varies in length; and, in addition, when the second single mode fiber 5 is elongated, the transmission speed of light passing through its interior changes as a result of Doppler effect.

Further, the amplitude of driving signal is adjusted so that the variation width of transmission time in this case corresponds with the time the beam requires for transmission of the light path when scanning a desired range.

Otherwise the second embodiment is similarly constructed to the first embodiment.

Basically the second embodiment operates in the same manner with the first embodiment, and further offers the same advantage as does the first embodiment.

(The third embodiment)

The first and second embodiments are so constructed as to meet the individual differences in light path length of beam scanning probes of one and the same type while this example can accept beam scanning probes having different lengths.

Figure 9:
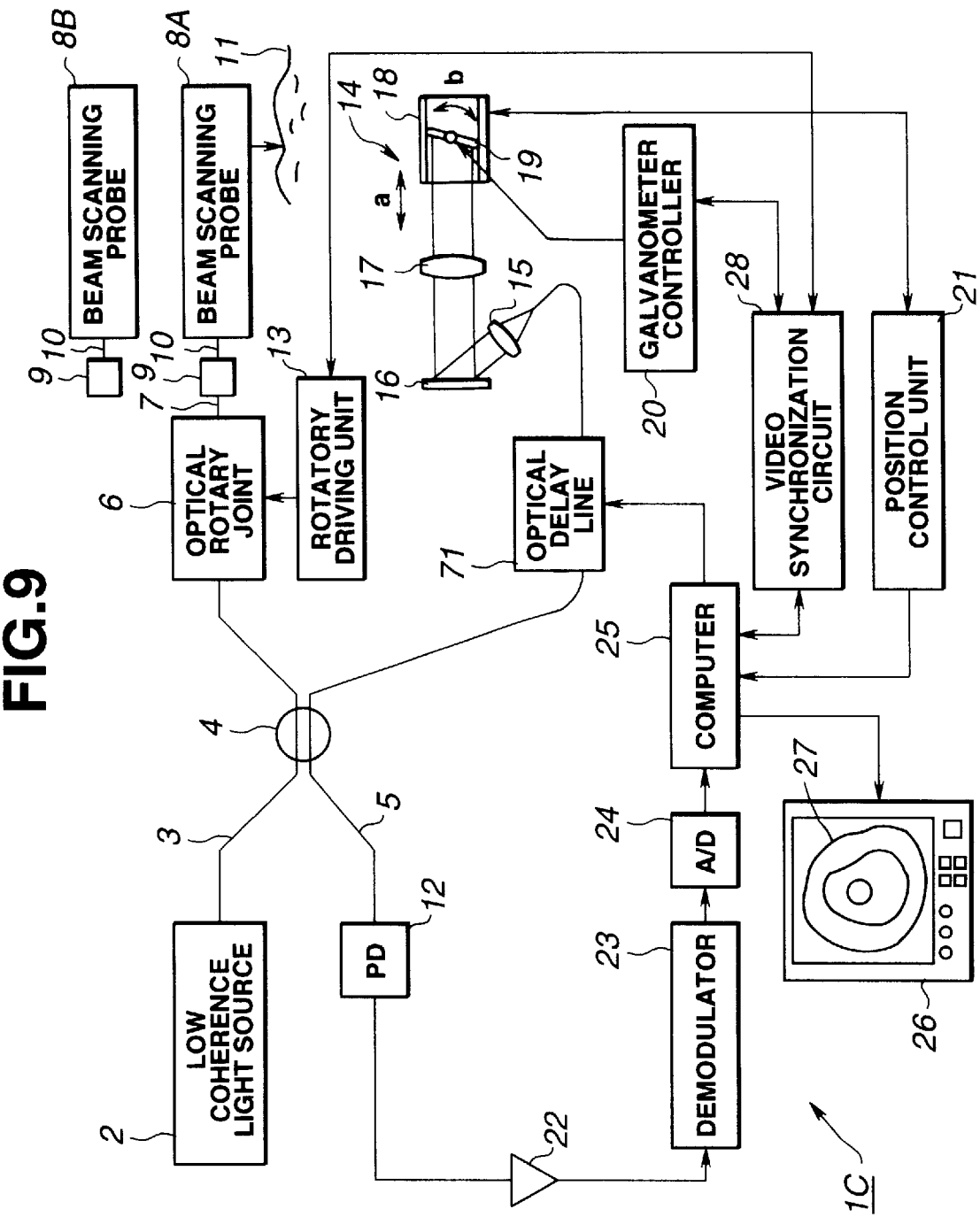
FIGS. 9 to 10 relate to the third embodiment of this invention.

The optical imaging apparatus 1C of the third embodiment as represented in FIG. 9 is obtained after modifying the optical imaging apparatus 1A as represented in FIG. 1 such that two different kinds of beam scanning probes 8A and 8B, instead of a single type of beam scanning probe 8, can be accepted, and this is achieved by adding an optical delay line 71, for example, to the outward end of second single mode fiber 5 in order to alter the light path in accordance with which one of beam scanning probes 8A and 8B is currently used. This optical delay line 71 is so constructed as to alter the length of light path in its interior under the instruction from the computer 25.

When in use, either of the beam scanning probes 8A and 8B is inserted into a channel of an appropriate endoscope; for example, when a bronchoscope is used to examine the state of bronchi, the beam scanning probe 8A having a total length of 1.5 m is employed, while a colonoscope is used to examine the large intestine, the beam scanning probe 8B having a total length of 3.0 m is employed.

Figure 10:
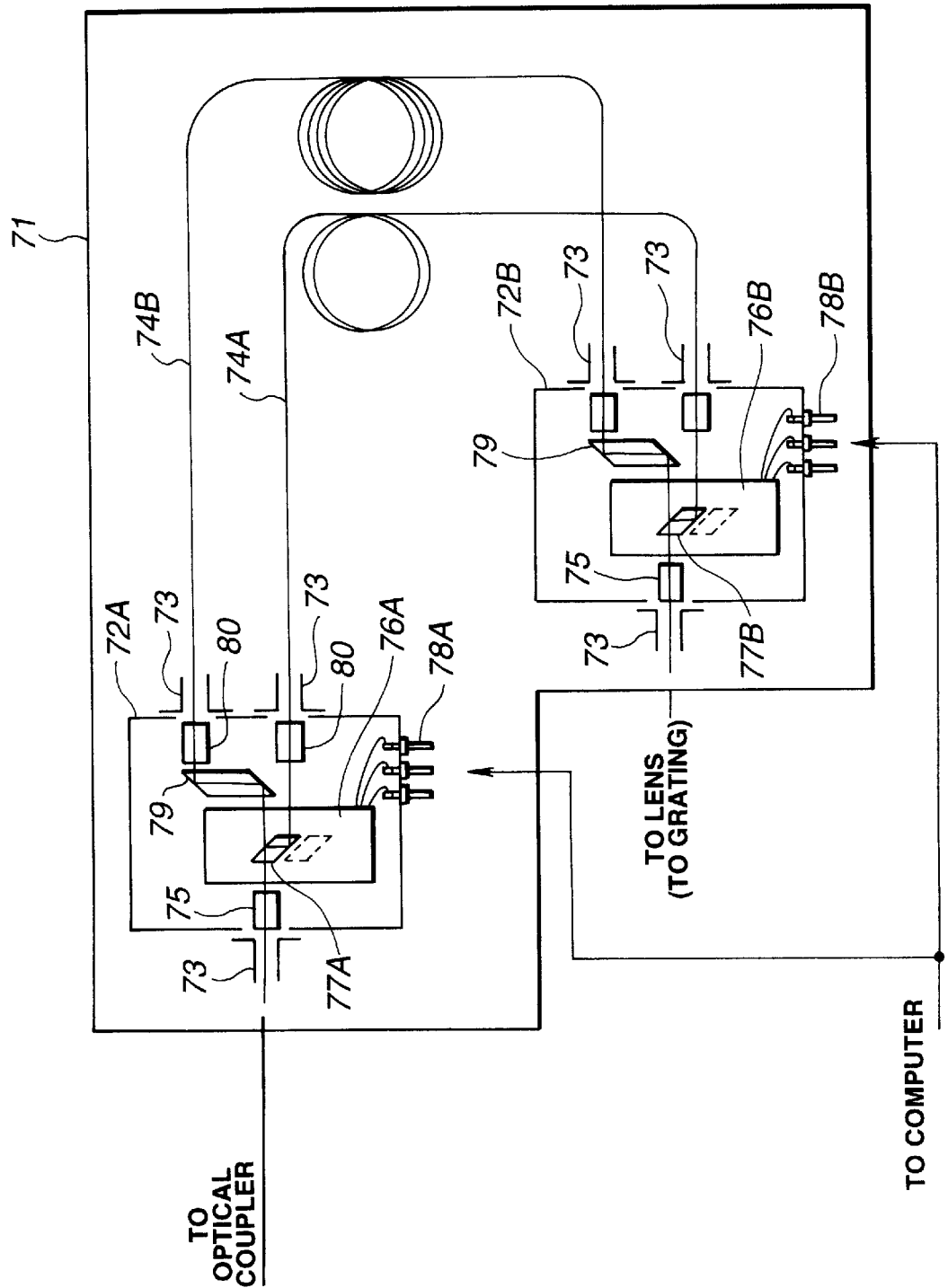

FIG. 10 gives the structure of an optical delay line 71. Optical switches 72A and 72B are inserted between the end of second single mode fiber 5 close to the optical coupler 4, and the lens 15; and the ends of involved paths are connected through receptacles 73 to the switches. Between these optical switches 72A and 72B are inserted two single mode fibers 74A and 74B having different light paths. For example, the single mode fiber 74B is longer than the single mode fiber 74A, and the difference in light path length between the two is so chosen as to be practically equal to the difference in light path length between the beam scanning probes 8A and 8B.

Further, the single mode fiber 74A is adjusted in its length such that the light path a beam would take after being split at the optical coupler 4, passing through the beam scanning probe 8, being reflected from a spot close to the surface of a biological tissue 11, and returning to the optical coupler 4, will become essentially equal to the light path a beam would take after passing through the single mode fiber 74A itself, being reflected by the light path modifying mechanism 14 and returning to the optical coupler 4.

The optical switch 72I (I can be either A or B) has a rod lens 75 placed opposite to the end of second single mode fiber 5; a driving mechanism 76I placed opposite to the rod lens 75 has a prism 77I; and being given a driving signal from the computer 25 via a terminal 78I the prism 77I can alter its position between the two limits respectively represented by solid and dotted lines.

When the prism 77I is placed opposite to the rod lens 75, a beam passing through the rod lens 75 placed opposite to the end of second single mode fiber 5 is reflected by this prism 77A, to be guided to the end of another single mode fiber 74A which is connected to the receptacle 73, via the rod lens 80 placed on the light path on the reflected side.

Alternatively, when the prism 77I is retreated from the position opposite to the rod lens 75, a beam passing through the rod lens 75 placed opposite to the end of second single mode fiber is incident, without touching the driving mechanism, on the prism 79; it is then reflected by the prism 79; and it is then guided via the rod lens 80 to the end of other single mode fiber 74B.

As seen from above, when a beam scanning probe 8A whose total length is short is connected, the single mode fiber 74A within the optical delay line 71 is selected; on the contrary when a beam scanning probe 8B whose total length is long is connected, the single mode fiber 74B within the optical delay 71 is selected. Through this operation it is possible to use the apparatus even when beam scanning probes 8A and 8B different in length are employed, in the same manner as if it incorporates a single type of beam scanning probes variable in their light path.

Although the above description is given assumed that the apparatus incorporates two kinds of beam scanning probes 8A and 8B different in length, the same description applies similarly to an apparatus incorporating three or more kinds of beam scanning probes.

(The fourth embodiment)

Although the first to third embodiments incorporate, in order to absorb individual light path differences of beam scanning probes, a second light path modifying means or, in a broader sense, a transmission time altering means on the light path for the reference beam, this example incorporates the same mechanism on the light path for the sample beam passing through the beam scanning probe.

Figure 11:
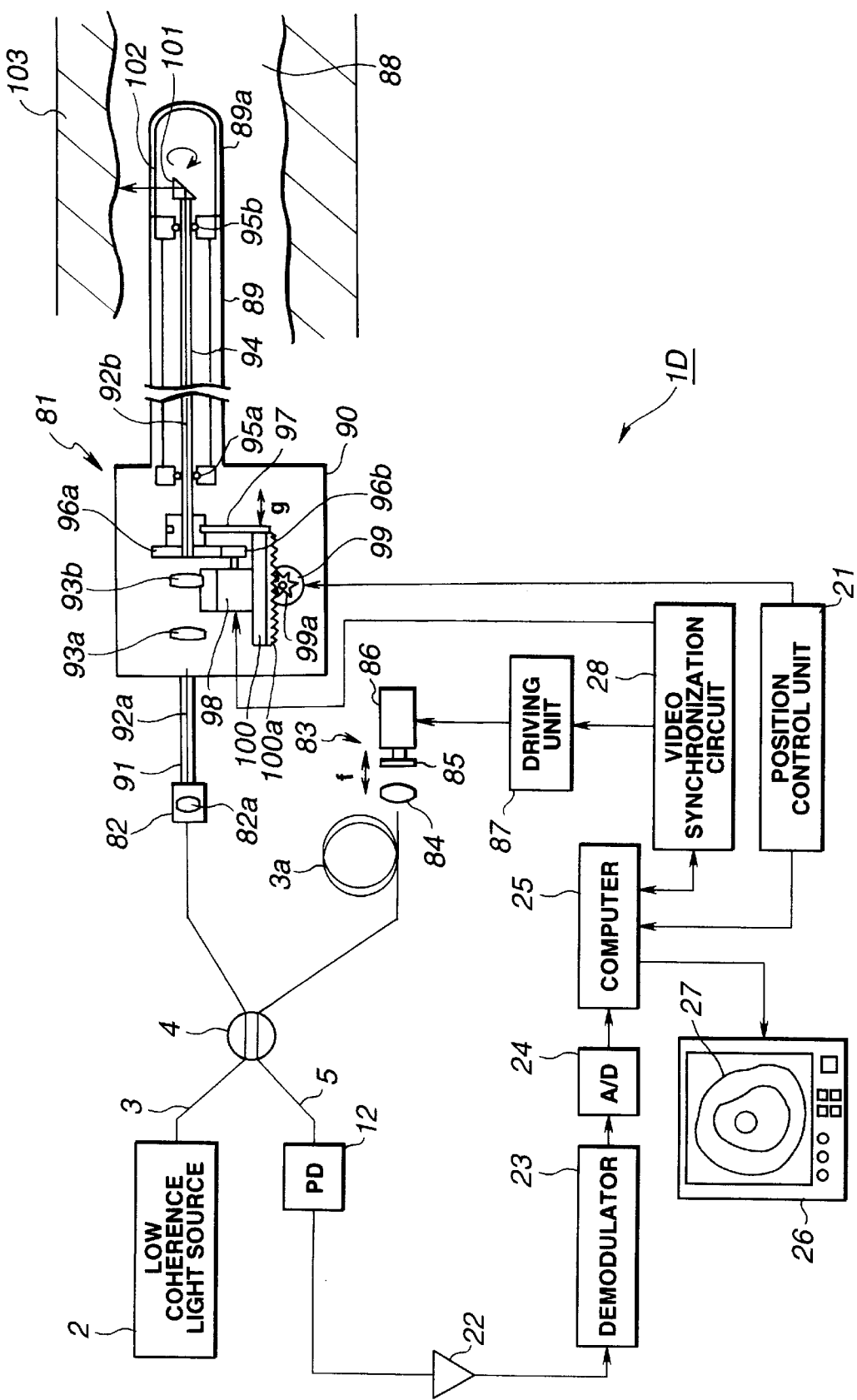
FIGS. 11 to 14 relate to the fourth embodiment of this invention.

The optical imaging apparatus 1D of the fourth embodiment as represented in FIG. 11 modifies the optical imaging apparatus 1A of FIG. 1 such that the first single mode fiber 3 has at its outward end a connector 82 incorporating a lens 82a of the beam scanning probe 81; the second single mode fiber 5 has a loop 3a midway on its outward end; and a light path modifying means 83 is placed opposite to the last-mentioned end.

This light path modifying means 83 consists, for example, of the lens 84, a mirror 85 placed opposite to that lens 84, and an actuator 86 to move the mirror 85 in the directions as indicated by symbol f. To this actuator is given a driving signal from a driving unit 87; and the mirror 85 moves at a high speed. Namely, this light path modifying means 83 serves as a first light altering means.

The beam scanning probe 81 has an insert 89 to be inserted into a bodily cavity 88; the insert 89 has a handle 90 at its rear end to be gripped by the operator; a cable 91 extends from this handle 90; the connector 82 at one end of this cable 91 is connected to one end of first single mode fiber 3; and by this means the single mode fiber 92a inserted through the hollow space of cable 91 is optically connected to the first single mode fiber 3.

A beam passing through this single mode fiber 92a is transmitted to the single mode fiber 92b inserted into the insert 89b via lenses 93a and 93b within the handle 90.

The single mode fiber 92b is introduced in a flexible shaft 94, and has its rear and front ends fixed to the flexible shaft 94. The flexible shaft 94 has its rear and front ends rotatably supported by bearings 95a and 95b respectively.

Further, the flexible shaft has its rear end fixed to a gear 96a; and the gear 96a is rotatably supported by a rotation supporting member 97. This gear engages with the gear 96b attached to a stepping motor 98 and is put into rotation being driven by the latter. This stepping motor 98 is fixed to a rack 100 attached to the under surface of a linear gear section 100a which engages with a pinion gear 99a attached to the motor 99; and it, being capable of freely moving in the directions as indicated by symbol g of FIG. 11, serves as a second light path modifying means. The rotation supporting member 97 has its lower end fixed to the rack 100.

To the outward tip of flexible shaft 94 is fixed a prism 101; it reflects a beam transmitted through the single mode fiber 92b in the direction perpendicular to the last light path; the beam passes through a transparent sheath 102 at the outward tip 89a; and it strikes on the wall surface 103 of a body cavity 88.

The driving unit 87 is connected to the video synchronization circuit 28, while the stepping motor 98 and the motor 99 are connected to the position control unit 21.

Otherwise the fourth embodiment is constructed similarly to the composition as represented in FIG. 1. In this example, the motor 99 drives the single mode fiber 92b and prism 101 in the beam scanning probe 81 to move along the central axis of single mode fiber 92b, and thus even when a currently used beam scanning probe 81 has a different light path from that of a previous one, it is possible to obtain images in the depth direction by rotating the motor in accordance with the difference in light path length in question and therewith moving the single mode fiber 92b by a sufficient distance to cancel out the difference.

It is also possible using the apparatus as depicted in FIG. 11 to obtain three dimensional tomographic images, when a second light path modifying means is introduced on the light path for the reference beam, by moving the rack 100 via the motor 99. Further, the connector 82 may be inserted between the insert 89 and handle 90 of beam scanning probe 81.

Figure 12:
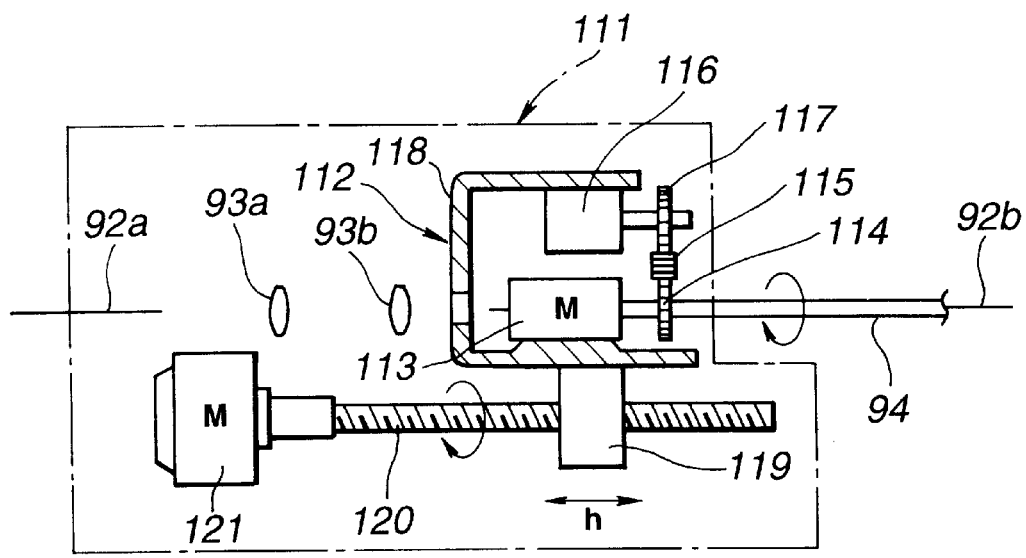

FIG. 12 shows the composition of driving section 111 stored in the handle of a first variation of the beam scanning probe 81 depicted in FIG. 11.

The unit depicted in FIG. 12 has the rear end of flexible shaft 94 fixed to the shaft of a motor 113 constituting a radial rotating section 112 within the driving section 111; and a gear 114 fixed to this shaft is coupled with another gear 117 fixed to a rotary encoder 116 via a third gear 115. The motor 113 and the rotary encoder 116 are fixed to a radial rotation supporting member 118; the radial rotation supporting member 118 is in turn fixed to a driving force transmitting member 119; the driving force transmitting member 119 receives in its threaded hole a pole screw axis 120; and the pole screw axis is jointed with a stepping motor 121. Thus, rotation of the stepping motor 121 will result in the movement of the radial rotating section 112 together with the driving force transmitting member 119 in the axial direction of pole screw axis 120, that is, in the directions as indicated by symbol h.

The single mode fiber 92b inserted through the flexible shaft 94 further penetrates the body of motor 113, passes through a hole prepared opposite on the wall of radial rotation supporting member 118, and faces lenses 93b and 93a; and thus it can receive/transmit beams from/into a single mode fiber 92a placed opposite to the lens 93a.

Figure 13:
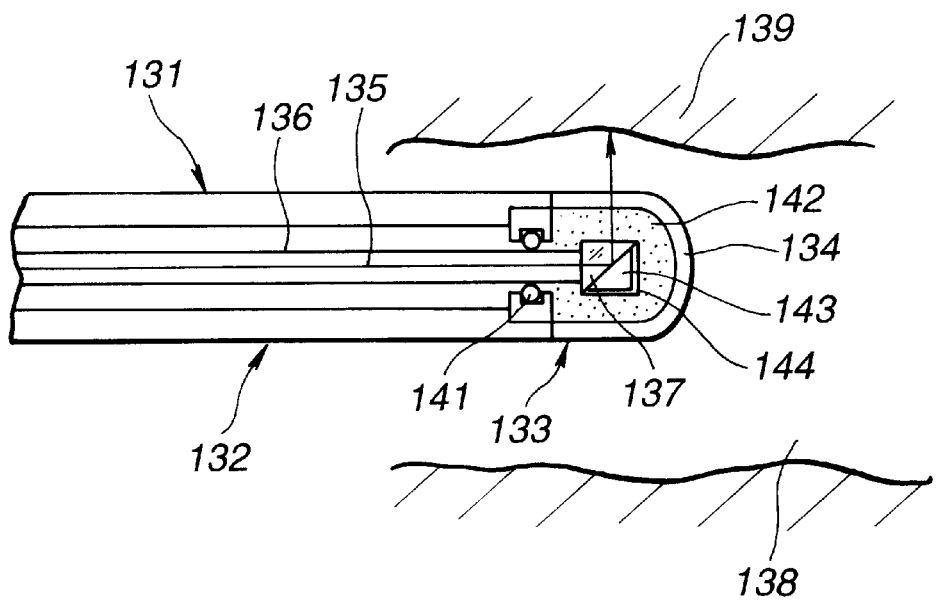

FIG. 13 shows the composition of the outward tip of a second variation of the beam scanning probe 81.

The beam scanning probe 131 of the second variation as depicted in FIG. 13 has the outward tip of insert 132 formed of a transparent sheath 134; into this insert 132 is placed a flexible shaft 136 containing a single mode fiber 135; the single mode fiber 135 is fixed to the tip of flexible shaft 136; a beam is reflected by an inclined surface prepared in a prism 137 fixed to the tip of flexible shaft 136 in the direction normal to the current light path; and the beam emanates as a low coherence light beam and heads towards the internal wall of a body cavity, and at the same time a reflected beam is sent back in the reverse direction.

An O-ring 141 caps the base of transparent sheath 134 to serve as a sealing means to prevent leakage of a liquid 142 such as glycerin or fluorinate filling the interior of transparent sheath 134. The liquid 142 such as glycerin or fluorinate has a refractive index comparable with that of prism 137, and thus filling the spaces around the light emanating and light receiving surfaces of prism 137 with such a liquid makes it possible to prevent the light transmission efficiency of prism 137 from lowering as a result of reflections at those interfaces.

Further, in a space adjacent to the reflective surface of prism 137 is prepared an air chamber 144 filled with air 143.

Hence, adjacent to the inclined reflective surface of prism 137 is formed a layer of air 143 having a smaller refractive index than does the prism 137, and thus an incident beam is totally reflected by the inclined reflective surface which will also result in improvement of light transmission efficiency. Alternatively, applying an aluminum coating on the reflective surface of prism 137 will dispense with the use of air layer 143.

Otherwise the fourth embodiment is similarly constructed to the beam scanning probe 81 of FIG. 11.

The low coherence light beam may have a wavelength within the infra-red region which has a good penetrating activity towards a biological tissue, or may have a wavelength within the visible region when only a shallow scanning is required.

Figure 14:
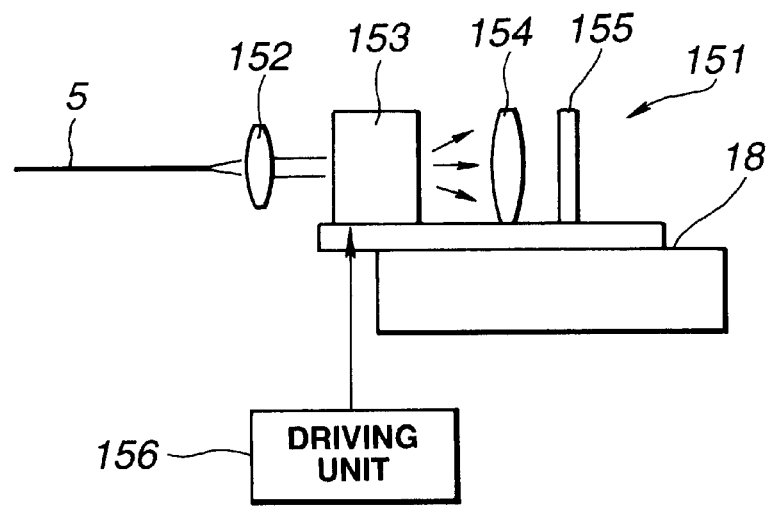

FIG. 14 shows the light path modifying mechanism 151 of a third variation. The light path modifying mechanism 151 has a lens 152 which is placed at the tip of second single mode fiber 5 of FIG. 1 to convert incident light into parallel rays; an acoustically modifiable beam deflector 153 which is mounted on the uniaxial stage 1, to deflect incident parallel rays in accordance with a periodic distribution of refractive indices in a three dimensional space of a transparent medium which is invoked by a sound wave passing therethrough; a lens 154 which is placed at the light emanating end of acoustically modifiable beam deflector which reconverts the emanating light into parallel rays; a mirror 155 to reflect the light passing through the lens 154; and a driving unit 156 which delivers a driving signal to the acoustically modifiable beam deflector 153.

The driving unit 156 can vary the deflection angle, by obtaining driving signals from a sweep oscillator which can vary the frequency of signals, applying the signals to, for example, a piezo element constituting the acoustically modifiable beam deflector 153, producing therewith a periodic distribution of refractive indices in a transparent medium such as air, and thus altering the pitch of diffraction grating. Being thus deflected, the light path a beam reflected by the mirror 155 would take or its transmission time changes. When this operation is repeated periodically at a high speed, it is possible to alter the light path or the transmission time sufficiently to achieve the scan of a desired range.

The driving unit 156 is also connected to the video synchronization circuit, and driving signals are repeated such that sweeping occurs in synchrony with the video synchronization signals.

(The fifth embodiment)

The fifth embodiment is practically the same with the first embodiment, and thus description will be limited to different features, and further description will be omitted. Similar constitutive elements are associated with the same symbols.

Figure 15:
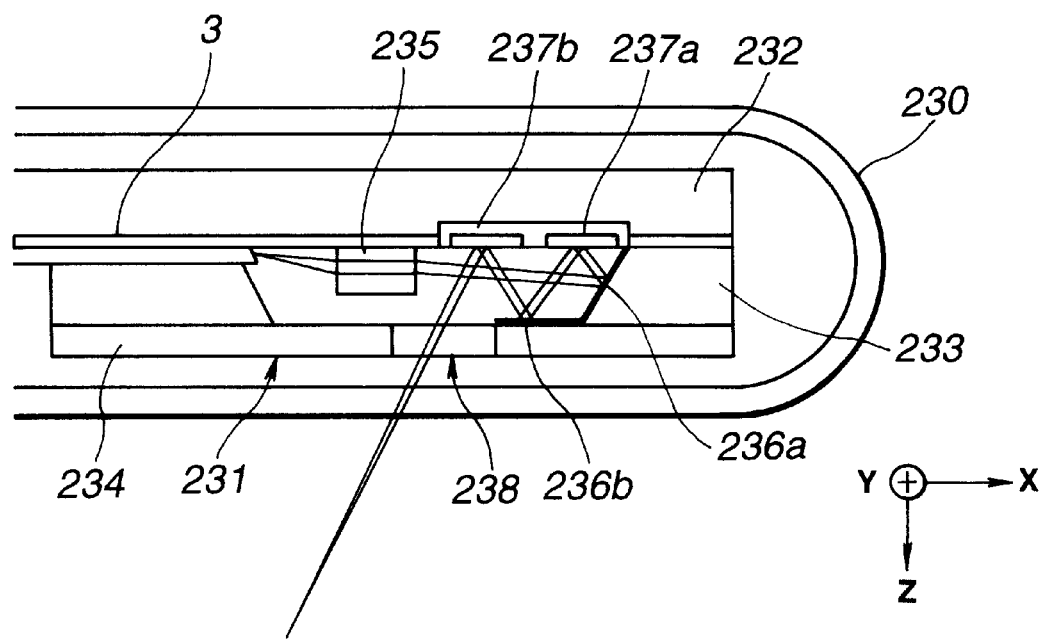
FIGS. 15 and 16 relate to the fifth embodiment of this invention.
Figure 16:
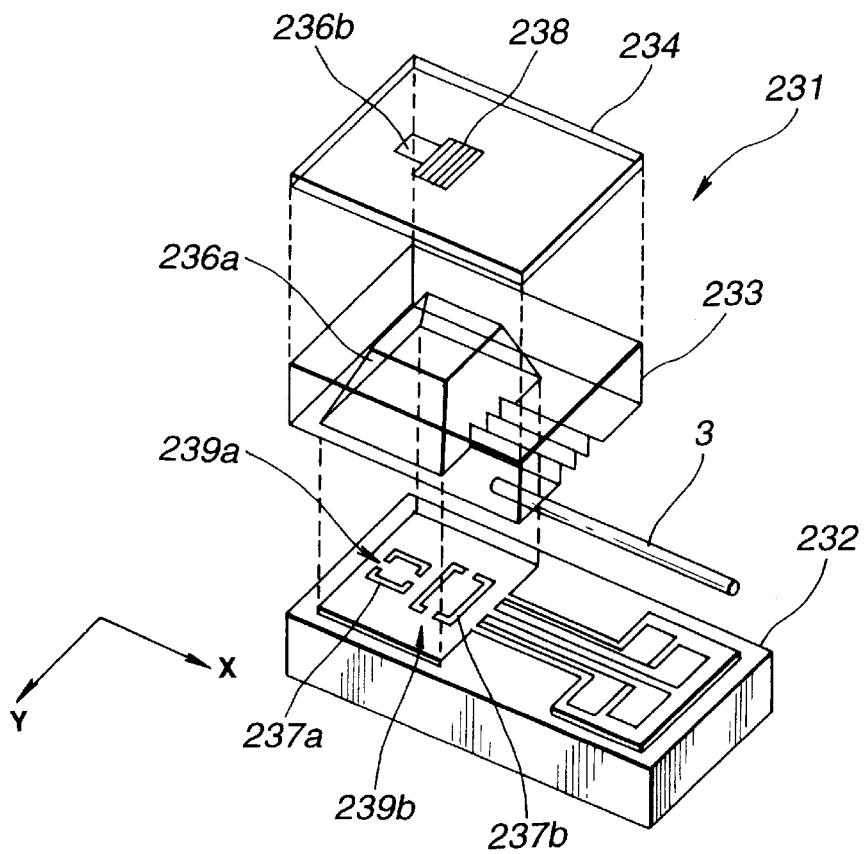

As shown in FIG. 15, the beam scanning probe 8 of this example covered with a sheath 230 has a scanning unit 231 to serve as a scanning means in its tip; as shown in FIG. 16 this scanning unit 231 is fabricated by the semiconductor fabrication technique, or for example by the technique which is utilized for the fabrication of a minute confocal microscope disclosed in the literature: "Micromachined scanning confocal optical microscope," OPTICS LETTERS, vol. 21, No. 10, May, 1996; and it is composed of a silicone substrate 232, a silicone spacer 233 and a optical window plate 234.

Turn to FIG. 15. The silicone spacer 233 constituting the scanning unit 231 includes the outward end surface of first single mode fiber 3, a GRIN (graduate index) lens 235, and first and second aluminum plated mirrors 236a and 236b; and a low coherence light beam emanating from the outward end surface of first single mode fiber 3 is reflected, after passing through the GRIN lens 235, by the first aluminum plated mirror 236a, and then by a first scanning mirror 237a placed on the silicone substrate 232. The low coherence light beam reflected by the first scanning mirror 237a is then reflected by the second aluminum plated mirror 236b, and further by the second scanning mirror 237b placed on the silicone substrate 232, and is directed via a window 238 prepared on the optical widow plate 234 towards a lesion (not illustrated here).

The first single mode fiber 3 is a single mode optical fiber, and acts as a pinhole, and the GRIN lens intervenes. Thus, only light reflected from the lesion under focus comes back to the outward end surface of first single mode fiber 3.

As shown in FIG. 16, the first and second scanning mirrors 237a and 237b placed on the silicone substrate can alter their angle to focus a low coherence light beam onto a lesion and to scan the former upon the latter; and they are supported by respective hinges 239a and 239b. These hinges 239a and 239b are made rotatable being driven by static electric forces along X- and Y-axes intersecting with each other at right angles as shown in the figure. The static electric forces are controlled by the rotation driving unit 13.

Otherwise the fifth embodiment is similarly constructed to the first embodiment.

(Effect)

Next, description will be given of the effect of this example having the constitution as described above.

In this example, the beam scanning probe 8 is inserted in the interior of a living body, and the tip of beam scanning probe 8 is placed close to a lesion.

Then, a low coherence light beam from the low coherence light source 2 is directed to the base surface of first single mode fiber 3; and the beam is transmitted by the optical coupler 4 to the outward ends of first single mode fiber 3 and of second single mode fiber 5.

The low coherence light beam emanating from the outward end of first single mode fiber 3 is scanned by the scanning unit 231 installed in the tip of beam scanning probe 8 over a two-dimensional surface represented by X-Y plane of FIG. 15.

Namely, a low coherence light beam emanating from the outward end surface of first single mode fiber 3 is reflected, after passing through the GRIN lens 235, by the first aluminum plated mirror 236a, and then by the first scanning mirror 237a placed on the silicone substrate 232. The low coherence light beam reflected by the first scanning mirror 237a is then reflected by the second aluminum plated mirror 236b, and further by the second scanning mirror 237b placed on the silicone substrate 232, and is directed via the window 238 prepared on the optical window plate 234 towards a lesion. The first and second scanning mirrors 237a and 237b are put into rotation with respective hinges 239a and 239b acting as rotation axes under the influence of static electricity provided and controlled by the rotation control unit 13, to scan the beam over a two-dimensional surface. Scanning of a low coherence light beam by the scanning unit 231 occurs at a resolution of about 10 $\mu$m.

On the other hand, another low coherence light beam emanating from the outward end surface of second single mode fiber 5 is reflected by the galvanometer mirror 19 mounted on the uniaxial stage 18; the low coherence light beam directed by the galvanometer mirror 19 towards the outward end surface of first single mode fiber 3 and emanating therefrom is scanned in the direction of Z-axis as represented in FIG. 15.

Namely, when the light path the reference beam reflected by the galvanometer 19 takes until it reaches the photo detector 12, and the light path the sample beam passing through the first single mode fiber 3 and reflected back from a certain depth of a lesion until it reaches the photo detector 12 become comparable, an interference takes place between the two on account of physical characteristics inherent to those low coherence light beams dependent on their light path length, and then an interference fringe is obtained characteristic with that depth. Accordingly, altering the light path of reference beam by adjusting the galvanometer mirror 19 makes it possible to obtain interference fringe data necessary for acquisition of tomographic images in the depth direction. Scanning of a low coherence light beam in this case occurs at a resolution of about 18 $\mu$m.

Signals, after having undergone a photo-electric conversion at the photo detector 16, are amplified by the amplifier 22. Then, they are delivered to the demodulator 23 in the signal processing unit 23 where signal components having the same frequency with the reference signal are extracted. The components thus extracted are rectified/amplified, converted by A/D converter 24 into digital signals, and delivered to the computer 25 where they receive various signal processings. Thus, a three-dimensional tomographic image dependent on low coherence light beams is displayed on the monitor 6.

Otherwise the fifth embodiment exerts the same effect as does the first embodiment.
(Advantage)

As seen from above, this example, in addition to providing the same advantages as in the first embodiment, makes it possible to perform two-dimensional scanning at a resolution of about 10 $\mu$m through the working of the scanning unit 231 by allowing the computer 25 to drive/control the scanning unit 231 and galvanometer mirror 19 via the rotation driving unit 13, and to obtain a three dimensional interference data by scanning a beam through the intervention of the galvanometer mirror 19 in the depth direction at a resolution of about 18 $\mu$m, thereby achieving the display of high-resolution three dimensional tomographic images on the monitor 26.

Hence, according to the beam scanning tomographic imaging apparatus of this example, the minutely fabricated scanning unit 231 prepared on the silicone substrate by the semiconductor fabrication technique is placed in the tip of the beam scanning probe 8 which is inserted into a body cavity to collect optical tomographic data of a lesion; and thus it is possible, in contrast with conventional optical tomographic imaging apparatuses dependent on mechanical scanning devices, to allow the beam scanning probe to have a slender tip, and thus to make a high-resolution three dimensional scanning.
(The sixth embodiment)

The sixth embodiment is practically the same with the fifth embodiment, and thus description will be limited to different features, and further description will be omitted. Similar constitutive elements are associated with the same symbols.
(Constitution)

Figure 17:
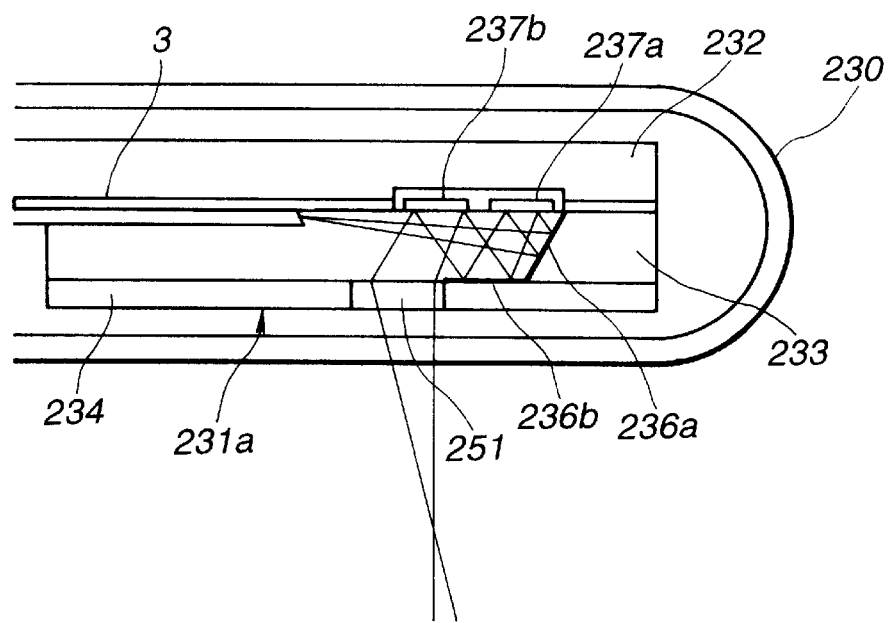
FIGS. 17 to 19 relate to the sixth embodiment of this invention.

As shown in FIG. 17, the scanning unit 231a installed in the tip of a beam scanning probe 8 of the sixth embodiment is composed of a confocal lens 251 placed at the window 238 which has a high focusing efficiency at very high NA, instead of the GRIN lens 235 of the fifth embodiment.

Figure 18:
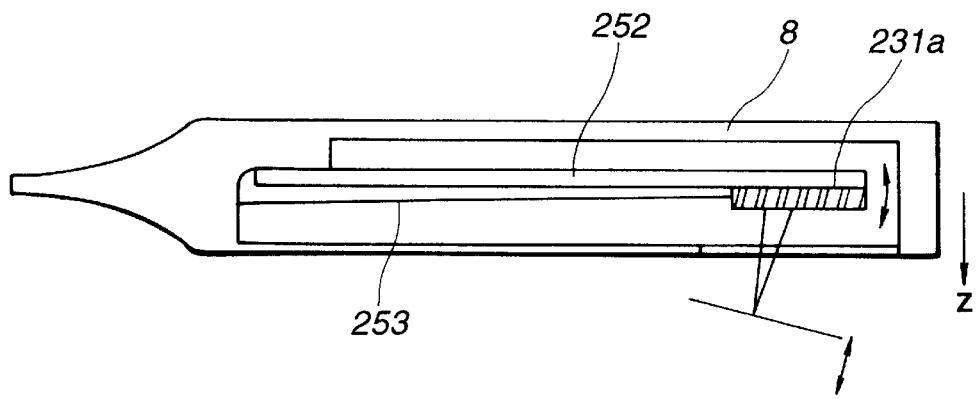

As further shown in FIG. 18, the scanning unit 231a is so constructed as to be driven in the direction of Z-axis by, for example, a bimorph type piezo-electric actuator 252, and, when a voltage is applied, the actuator actuates the scanning unit 231a towards a lesion. This piezo-electric actuator 252 is bonded to the interior of beam scanning probe 8; and it is connected via a electric cable 253 to the rotation driving unit 13.

Other constitutive features are the same with those of the fifth embodiment.
(Effect)

Like the fifth embodiment, the beam scanning probe 8 is inserted in a living body, and the tip of beam scanning probe 8 is placed close to a lesion. In this state, with this example, the scanning unit 231 is displaced towards the lesion by the piezo-electric actuator 252 of FIG. 18, and the scanning position of scanning unit 231a with respect to the lesion is adjusted.

Then, in the same manner as in the fifth embodiment, a low coherence light beam from the low coherence light source 2 is directed to the base surface of first single mode fiber 3; and the beam is transmitted by the optical coupler 4 to the outward ends of first single mode fiber 3 and of second single mode fiber 5. The low coherence light beam emanating from the outward end of first single mode fiber 3 is scanned by the scanning unit 231 installed in the tip of beam scanning probe 8 over a two-dimensional surface. On the other hand, another low coherence light beam emanating from the outward end surface of second single mode fiber 5 is reflected by the galvanometer mirror 19; the low coherence light beam directed by the galvanometer mirror 19 towards the outward end surface of first single mode fiber 3 and emanating therefrom is scanned in the direction of depth of the lesion.

During this operation, it is possible for this example to obtain a sharp relative signal output because individual light converging efficiencies of a confocal lens are accumulated, as compared with the relative signal output of the fifth embodiment which scans the low coherence light beam by directing it to the galvanometer mirror 19 via GRIN lens.

Other effects are the same with those of the first embodiment.

(Advantage)

Figure 19:
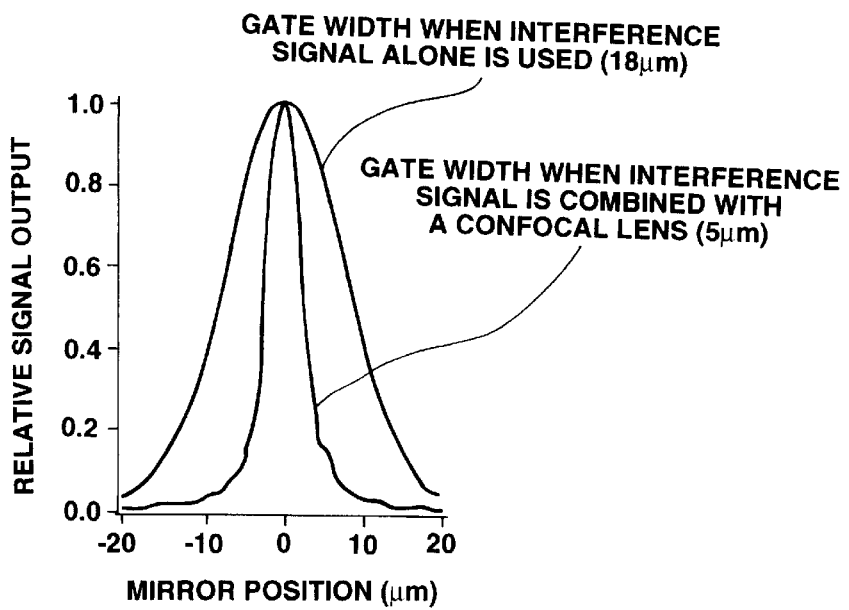

To put it briefly, this example, in addition to providing the same advantages as in the first embodiment, makes it possible to contract the gate width for a low coherence light beam to about 5 μm, instead of about 18 μm of the fifth embodiment, by incorporating a confocal lens 251 which has an excellent light converging efficiency as shown in FIG. 19, and to permit a high resolution scanning in the direction of depth of the lesion.

(The seventh embodiment)

The seventh embodiment is practically the same with the first embodiment, and thus description will be limited to different features, and further description will be omitted. Similar constitutive elements are associated with the same symbols.

This example consists of attaching a rotatory driving means on the outward tip of beam scanning probe 8I, thereby to perform a beam scanning.

Figure 20:
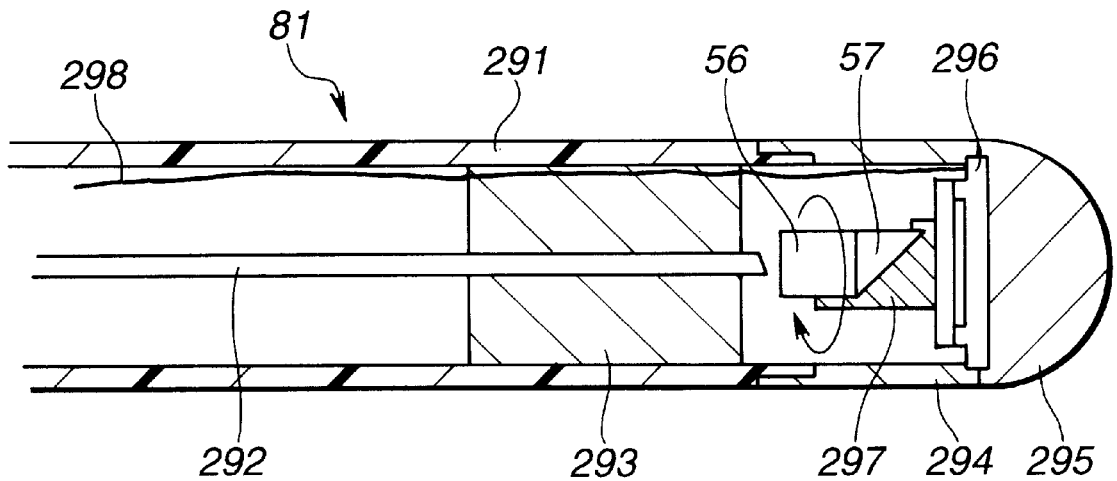
FIGS. 20 and 21 relate to the seventh embodiment of this invention.

As shown in FIG. 20, a single mode fiber 292 is inserted through a cylindrical sheath 291 which serves as the insert of beam scanning probe 8I, for example, along its central axis; and the outward end of the single mode fiber 292 passes through a central hole prepared on the columnar tip body 293 and fixed there being bonded with an adhesive or the like. The tip body 293 has its outer wall bonded to the inner surface of the tip of sheath 291.

To the tip opening of sheath 291, is firmly fitted the opening prepared on one (basic) end of a cylindrical, hard and transparent pipe 294; and the other (front) end of the transparent pipe 294 is capped by a semicircular frontal cap 295 for closure.

In the interior of frontal cap 295 is firmly fixed the stator of a supersonic motor 296, and to the rotatable rotor are fixed a micro prism 57 and a GRIN lens 56 via a support 297.

A lead wire 298 connected to the supersonic motor 296 is inserted into the sheath 291, and connected on the front side to a driving circuit not illustrated here. When power is switched on, a driving signal is provided to the supersonic motor 296, to put the rotor of supersonic motor 296 into rotation, and the micro prism 57 and GRIN lens 56 fixed to the support 97 are rotated together as indicated by the arrow.

A low coherence light beam guided by the single mode fiber 292 and emanating from its outward end surface, is converged by GRIN lens 56 placed opposite to that outward end surface and put into rotation, and the beam is reflected by the inclined surface of micro prism 57 to radiate in the direction normal to the central axis of bean scanning probe 8I.

This example can include an optical imaging apparatus where the beam scanning probe 8I has its basic end connected directly to one end of first single mode fiber 3, without the intervention of an optical rotary joint 6.

According to this example, it is possible to obtain practically the same advantages as provided by the first embodiment, not by resorting to a rotating single mode fiber 292 inserted through the beam scanning probe 8I, but by rotating instead GRIN lens and micro prism 57 placed opposite to the outward end of the same fiber.

When it is required to rotate the single mode fiber 292 as well via a rotation force transmitting member such as a flexible shaft, it becomes often difficult to smoothly transmit a rotation at hand to the tip without any delay especially when the insert of an endoscope is tortuously introduced into a body cavity and a forceps channel within similarly takes a tortuous course. In such a case, the displacement in association with rotation at hand may be different from that at the tip.

In such a case, as long as the displacement remains constant, image quality will be scarcely affected. By contrast, when the displacement occurs locally, namely, when the angular velocity changes according to the angle around the center, and when image acquisition is based on the rotation at hand, the error will be exaggerated and the quality of resulting tomographic images will deteriorate.

With this example, even when an endoscope is inserted into a sinuous body cavity, the rotation remains unaffected (because the tip includes the supersonic motor 296, the load in association with rotation is essentially constant, and rotation proceeds at a constant speed), and thus detection of rotation position can be achieved from driving signals without resorting to the rotation of some mechanical element.

Hence, this example, although being constructed rather simply, is advantageous in that it is possible to have a slender insert, perform a stable beam scanning, and thus obtain stable tomographic images.

Further it is possible with this example to more effectively prevent the fracture of a single mode fiber 292 than is possible with the apparatus where a single mode fiber 292 itself inserted through beam scanning probe 8I is put into rotation.

Turn to FIG. 20. The GRIN lens 56 may be fixed to the tip body 293, and the micro prism 57 alone be mounted on the support 297; and the supersonic motor 296 may rotate only the micro prism 57. In this case, the load in association with rotation is reduced; thus it is only necessary for a supersonic motor 296 to give a rather small rotational force; and the apparatus may be compacted. Or, a faster beam scanning may be possible.

Figure 21:
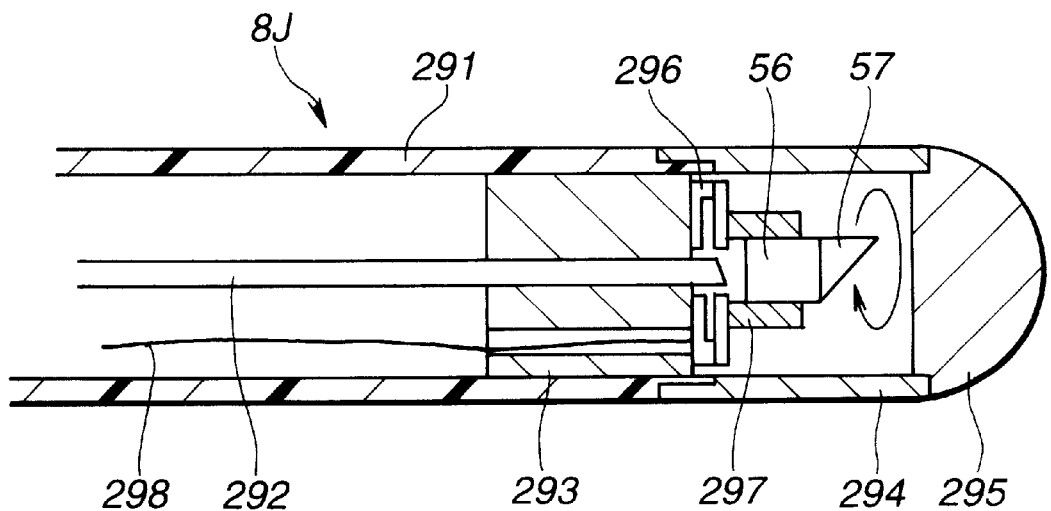

FIG. 21 shows the tip of a variant beam scanning probe 8J. With this variant example, the stator of a supersonic motor 296 having a hole to receive a single mode fiber 292 is bonded to the apical surface of the tip body 293; and a micro prism 57 and a GRIN lens 56 are attached to the rotor via a cylindrical support 297.

Further, the hole for lead wire insertion prepared on the tip body 293 passes a lead wire 298 connected to the supersonic motor 296. Otherwise, this example is similarly constructed to the seventh embodiment. This variation has essentially the same effect and advantage with those of the seventh embodiment as described above.

The compositions resulting from combining the constituents of above examples in various ways also belong to this invention.

Obviously it is possible to derive from the description of this invention various variants in a wide variety of fields without departing from the spirit and scope of this invention. This invention, only restricted by the specifications given in the attached claims, is not limited by any particular examples.

What is claimed is:

1. An optical imaging apparatus comprising:
  a light source to generate a low coherence light beam;
  an optical probe which incorporates a sample beam transmitter which includes a single mode fiber to transmit a sample beam containing the low coherence light beam to a test sample, and to also transmit the sample beam upon being reflected by the test sample;
  a coupler which is detachably connectable to the optical probe via an optical connector and which allows the reflected sample beam and a reference beam containing the low coherence light beam to interfere with each other;

a detector which detects the interfering beams;

an image signal generator to generate image signals on the basis of signals detected by the detector;

a first transmission time altering unit which alters the transmission time of the reference beam in accordance with a scan range of the optical probe so that the interference between the reflected beam and the reference beam takes place within the scan range in the axial direction with respect to the optical light paths of the sample beam and the reference beam, and a second transmission time altering unit to alter the transmission time of the reference beam in accordance with a light path length of the sample beam transmitter.

2. The optical imaging apparatus of claim 1, wherein the coupler functions as a low coherence light beam splitter to split the low coherence light beam generated by the light source to form the sample beam and the reference beam; and the low coherence light beam splitter transmits the sample beam via the optical connector to the sample beam transmitter of the optical probe and transmit the reference beam to the first transmission time altering unit and the second transmission time altering unit.

3. The optical imaging apparatus of claim 2, wherein the low coherence light beam splitter is optically connected to one end of each of a first through a fourth single mode fiber;

the other end of the first single mode fiber is optically connected to the light source;

the other end of the second single mode fiber is optically connected to the sample beam transmitter;

the other end of the third single mode fiber is optically connected to the first transmission time altering unit and the second transmission time altering unit; and the other end of the fourth single mode fiber is optically connected to the detector which detects an interference between the reflected beam and the reference beam.

4. The optical imaging apparatus of claim 1, further comprising a third transmission time altering unit to alter the transmission time of the reference beam in accordance with the light path of sample beam transmitter.

5. The optical imaging apparatus of claim 4, wherein the coupler functions as a low coherence light beam splitter to split the low coherence light beam generated by the light source into the sample beam and the reference beam; and the low coherence light beam splitter transmits the sample beam via the optical connector to the sample beam transmitter of the optical probe and transmits the reference beam to the first transmission time altering unit, the second transmission time altering unit, and the third transmission time altering unit.

6. The optical imaging apparatus of claim 4, wherein the third transmission time altering units includes an optical delay section to alter the transmission time of the reference beam by switching to a particular delay time among a plurality of predetermined delay times in accordance with a given type of optical probe.

7. The optical imaging apparatus of claim 5, wherein the third transmission time altering unit includes an optical delay section to alter the transmission time of the reference beam by switching to a particular delay time among a plurality of predetermined delay times in accordance with a given type of optical probe.

8. The optical imaging apparatus of claim 5, wherein the low coherence light beam splitter is optically connected to one end of each of a first through a fourth single mode fibers;

the other end of the first single mode fiber is optically connected to the light source;

the other end of second single mode fiber is optically connected to the sample beam transmitter;

the other end of third single mode fiber is optically connected to the first transmission time altering unit, the second transmission time altering unit, and the third transmission time altering unit; and the other end of fourth single mode fiber is optically connected to the detector which detects an interference fringe between the reflected beam and the reference beam.

9. The optical imaging apparatus of claim 6, wherein the optical delay section includes a combination of optical switches and a plurality of single mode fibers having different respective lengths.

10. The optical imaging apparatus of claim 7, wherein the optical delay section includes a combination of optical switches and a plurality of single mode fibers having different respective lengths.

11. The optical imaging apparatus of claim 1, wherein the first and second transmission time altering units include a galvanometer moving mirror and a uniaxial moving stage, respectively.

12. The optical imaging apparatus of claim 1, wherein the first transmission time altering unit is a combination of a piezo element and a single mode fiber; and the second transmission time altering unit is a uniaxial moving stage.

13. The optical imaging apparatus of claim 1, wherein the first transmission time altering unit is a galvanometer moving mirror; and the second transmission time altering unit is a combination of a light reflecting member and a uniaxial moving stage.

14. The optical imaging apparatus of claim 1, wherein the optical probe is a slender, soft and cylindrical sheath which can be inserted into a forceps channel of an endoscope.

15. The optical imaging apparatus of claim 14, further comprising:

a freely rotatable flexible shaft; and a single mode fiber within the sheath to scan a beam by rotation in the radial direction of the sheath; and a detachable optical connector on the proximal end of the fiber.

16. The optical imaging apparatus of claim 1, wherein the first transmission time altering unit is capable of rapidly altering the transmission time of the reference beam in accordance with the scan range.

17. The optical imaging apparatus of claim 1, wherein the first transmission time altering unit is capable of rapidly and periodically altering the transmission time of the reference beam in accordance with the scan range.

18. The optical imaging apparatus of claim 1, wherein the second transmission time altering unit is so adjustable as to be capable of altering the transmission time of the reference beam within a range defined a target portion of a test object so that tomographic images of that portion may be obtained.

19. An optical imaging apparatus comprising:

a light source to generate a low coherence light beam;

an optical probe which incorporates a sample beam transmitter which includes a single mode fiber to transmit a sample beam containing the low coherence light beam to a test sample and to transmit the sample beam upon being reflected by the test sample;

a coupler which is detachably connectable to the optical probe via an optical connector and which allows the reflected sample beam and a reference beam containing the low coherence light beam to form an interference fringe:

a detector which detects the interference fringe;

an image signal generator to generate image signals on the basis of signals detected by the detector;

a first transmission time altering unit which alters the transmission time of the reference beam in accordance with a scan range of the optical probe so that the interference between the reflected beam and the reference beam takes place within the scan range in the axial direction with respect to the optical light paths of the sample beam and the reference beam; and a second transmission time altering unit to alter the transmission time of the reference beam in accordance with a light path length of the sample beam transmitter.

20. The optical imaging apparatus of claim 19, wherein the coupler functions as a low coherence light beam splitter to split the low coherence light beam generated by the light source into the sample beam and the reference beam; and the low coherence light beam splitter transmits the sample beam via the second transmission time altering unit and the optical connector to the sample beam transmitter of the optical probe and transmits the reference beam to the first transmission time altering unit.

21. The optical imaging apparatus of claim 20, wherein the low coherence light beam splitter is optically connected to one end of each of a first through a fourth single mode fiber;

the other end of the first single mode fiber is optically connected to the light source;

the other end of the second single mode fiber is optically connected to the sample beam transmitter;

the other end of the third single mode fiber is optically connected to the first transmission time altering unit; and the other end of the fourth single mode fiber is optically connected to the detector which detects an interference between the reflected beam and the reference beam.

22. An optical imaging apparatus comprising:

a light source to generate a low coherence light beam;

an optical probe which incorporates a sample beam transmitter which includes a single mode fiber to transmit a sample beam containing the low coherence light beam to a test sample and to transmit the sample beam upon being reflected by the test sample;

a coupler which is detachably connectable to the optical probe via an optical connector and which allows the reflected sample beam and a reference beam containing the low coherence light beam to form an interference fringe;

a detector which detects the interference fringe;

an image signal generator to generate image signals on the basis of signals detected by the detector;

a first transmission time altering unit which alters the transmission time of the reference beam in accordance with a scan range of the optical probe so that the interference between the reflected beam and the reference beam takes place within the scan range in the axial direction with respect to the optical light paths of the sample beam and the reference beam; and a second transmission time altering unit to alter the total transmission time of the low coherence light beam and the reflected beam in accordance with a light path length of the sample beam transmitter.

23. The optical imaging apparatus of claim 22 wherein the optical probe a rotatable prism mirror in the tip thereof to reflect the sample beam in radial directions, fluid storing section disposed on the back side of a reflective surface of the prism mirror, and a fluid with a low refractive index stored in the fluid storing section.

24. The optical imaging apparatus of claim 23, wherein the fluid with a low refractive index is air.

25. The optical imaging apparatus of claim 1, wherein the optical probe has a sufficiently slender insert so as to be introducible into a test sample body; the probe includes:

at least one beam scanning elements affixed to a silicone substrate inserted at the tip of the insert in order to scan the sample beam transmitted via the sample beam transmitter over the test sample; and at least one lenses inserted at the tip of the insert in order to focus the sample beam transmitted via the sample beam transmitter onto the test sample, and to direct the sample beam upon being reflected by the test sample.

26. The optical imaging apparatus of claim 25, wherein the at least one beam scanning elements are activated through a static electrical force or a magnetic force.

27. The optical imaging apparatus of claim 25, wherein the at least one beam scanning elements includes two scanning elements to scan the sample beam in a two-dimensional plane tangential to the surface of the test sample.

28. The optical imaging apparatus of claim 25, wherein the at least one lens is inserted between the sample beam transmitter and the at least one beam scanning elements.

29. The optical imaging apparatus of claim 25, wherein the at least one lens is inserted between the at least one beam scanning elements and the test sample.

30. The optical imaging apparatus of claim 29, wherein the at least one lens, the at least one beam scanning elements and the sample beam transmitter are integratively combined to form a beam radiating section, the beam radiating section further including:

means to change the position of the beam radiating section in order to alter the distance between the at least one lens and the test sample.

31. The optical imaging apparatus of claim 1, wherein the optical probe comprises:

a slender, soft and cylindrical sheath with a blunt tip which can be introduced into a forceps channel of an endoscope, and which has at least the lateral wall of its tip made of a material which is transmissive to light;

a lens which is fixed towards the tip of the sample beam transmitter to focus the sample beam emanating from the sample beam transmitter at a specific position;

an ultrasonic motor installed in the interior of the tip of the sheath and including a rotor;

a power source to supply electricity to the ultrasonic motor and a controller therefor;

light path modifying unit fixed to the rotor of the ultrasonic motor to alter the light path of a light beam passing through the lens through the rotation of the ultrasonic motor.

32. The optical imaging apparatus of claim 31, wherein the sheath comprises a soft tube which is open at both ends, and a cap which is transmissive to light, the cap being attached to one end of the tube.

33. The optical imaging apparatus of claim 31, wherein the material of the sheath is formed from a material selected from the group consisting of polymethyl pentane, polyamide, FEP, TPFE or PFA.

34. The optical imaging apparatus of claim 31, wherein the sheath comprises a soft tube which is open at both ends, a pipe made of a material which is transmissive to light and connected to one end of the tube, and a cap enclosed in one end of the pipe.

35. The optical imaging apparatus of claim 34, wherein the pipe is made of fused quartz.

* * * * *

UNITED STATES PATENT AND TRADEMARK OFFICE
CERTIFICATE OF CORRECTION

PATENT NO : 6,069,698
DATED : May 30, 2000
INVENTOR(S) : Takeshi Ozawa et al.

It is certified that error appears in the above identified patent and that said Letters Patent are hereby corrected as shown below.

On the front page of the patent:

At Item [30], Foreign Application Priority Data, change second item, "Aug. 28, 1997 [JP] Japan....9-233000" to read:

--Aug. 28, 1997 [JP] Japan .........9-233001--.

Signed and Sealed this

Third Day of April, 2001

*Attest:*

NICHOLAS P. GODICI

*Attesting Officer*   *Acting Director of the United States Patent and Trademark Office*